(12) United States Patent
Angel et al.

(10) Patent No.: US 7,364,568 B2
(45) Date of Patent: Apr. 29, 2008

(54) MICRONEEDLE TRANSDERMAL TRANSPORT DEVICE

(75) Inventors: Aimee B. Angel, Atherton, CA (US); Ian W. Hunter, Lincoln, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 696 days.

(21) Appl. No.: 10/278,049

(22) Filed: Oct. 21, 2002

(65) Prior Publication Data

US 2003/0083619 A1 May 1, 2003

Related U.S. Application Data

(60) Provisional application No. 60/399,489, filed on Jul. 29, 2002, provisional application No. 60/338,425, filed on Oct. 26, 2001.

(51) Int. Cl.
*A61M 5/00* (2006.01)
*A61M 5/32* (2006.01)

(52) U.S. Cl. .................. 604/173; 604/174; 604/175

(58) Field of Classification Search ............ 604/890.1, 604/21–22, 35, 48, 504, 513, 65–66, 115, 604/128, 133, 139, 140–141, 143, 145, 153, 604/156, 173, 176, 239, 258, 272
See application file for complete search history.

(56) References Cited

U.S. PATENT DOCUMENTS

| | | | |
|---|---|---|---|
| 3,537 A | 4/1844 | Dodd | |
| 1,934,046 A | 11/1933 | Demarchi | |
| 2,088,780 A | 8/1937 | Follese | |
| 2,763,935 A | 9/1956 | Whaley et al. | |
| 2,945,496 A | 7/1960 | Fosdal | |
| 3,505,993 A | 4/1970 | Lewes et al. | |
| 3,568,735 A | 3/1971 | Lancaster | |
| 3,659,600 A | 5/1972 | Merrill | |
| 3,727,614 A | 4/1973 | Kniazuk | |
| 3,738,493 A | 6/1973 | Cummins et al. | |
| 3,814,097 A | 6/1974 | Ganderton et al. | |
| 3,894,538 A | 7/1975 | Richter | |
| 3,923,060 A | 12/1975 | Ellinwood, Jr. | |
| 3,964,482 A | 6/1976 | Gerstel et al. | |
| 4,140,109 A | 2/1979 | Savic et al. | |
| 4,394,231 A | 7/1983 | Nicolas | |
| 4,447,225 A | 5/1984 | Taff et al. | |
| 4,505,710 A | 3/1985 | Collins | |
| 4,619,652 A | 10/1986 | Eckenhoff et al. | |

(Continued)

FOREIGN PATENT DOCUMENTS

DE  44 20 232  12/1995

(Continued)

*Primary Examiner*—Catherine S. Williams
(74) *Attorney, Agent, or Firm*—Hamilton Brook Smith & Reynolds, P.C.

(57) ABSTRACT

A transdermal transport device includes a reservoir for holding a formulation of an active principle, and a needle with a bore extending along the length of the needle from a first end of the needle to a second end of the needle. The second end is substantially aligned to a plane parallel to a body surface of a biological body when the device is placed on the body surface. The device also includes an actuator which pumps the formulation through the bore of the needle between a target area of the body and the reservoir.

50 Claims, 14 Drawing Sheets

U.S. PATENT DOCUMENTS

| | | |
|---|---|---|
| 4,685,466 A | 8/1987 | Rau |
| 4,777,599 A | 10/1988 | Dorogi et al. |
| 4,808,156 A | 2/1989 | Dean |
| 4,886,499 A | 12/1989 | Cirelli et al. |
| 4,989,614 A | 2/1991 | Dejter, Jr. et al. |
| 5,062,834 A | 11/1991 | Gross et al. |
| 5,092,901 A | 3/1992 | Hunter et al. |
| 5,156,591 A | 10/1992 | Gross et al. |
| 5,225,750 A | 7/1993 | Higuchi et al. |
| 5,250,023 A | 10/1993 | Lee et al. |
| 5,262,128 A | 11/1993 | Leighton et al. |
| 5,279,544 A | 1/1994 | Gross et al. |
| 5,312,456 A * | 5/1994 | Reed et al. ............... 411/456 |
| 5,320,607 A | 6/1994 | Ishibashi |
| 5,354,273 A | 10/1994 | Hagen |
| 5,364,374 A | 11/1994 | Morrison et al. |
| 5,389,222 A | 2/1995 | Shahinpoor |
| 5,423,809 A | 6/1995 | Klicek |
| 5,425,706 A | 6/1995 | Gross et al. |
| 5,478,315 A | 12/1995 | Brothers et al. |
| 5,478,328 A | 12/1995 | Silverman et al. |
| 5,520,633 A | 5/1996 | Costin |
| 5,527,288 A | 6/1996 | Gross et al. |
| 5,533,995 A | 7/1996 | Corish et al. |
| 5,578,495 A | 11/1996 | Wilks |
| 5,591,139 A | 1/1997 | Lin et al. |
| 5,599,345 A | 2/1997 | Edwards et al. |
| 5,611,806 A | 3/1997 | Jang |
| 5,649,423 A | 7/1997 | Sniegowski |
| 5,697,901 A | 12/1997 | Eriksson |
| 5,785,688 A | 7/1998 | Joshi et al. |
| 5,827,216 A | 10/1998 | Igo et al. |
| 5,843,016 A | 12/1998 | Lugnani et al. |
| 5,848,991 A | 12/1998 | Gross et al. |
| 5,855,801 A | 1/1999 | Lin et al. |
| 5,879,326 A | 3/1999 | Godshall et al. |
| 5,928,194 A | 7/1999 | Maget |
| 5,928,207 A | 7/1999 | Pisano et al. |
| 5,957,895 A | 9/1999 | Sage et al. |
| 5,964,729 A | 10/1999 | Choi et al. |
| 5,971,998 A | 10/1999 | Russell et al. |
| 5,972,013 A | 10/1999 | Schmidt |
| 5,983,136 A | 11/1999 | Kamen |
| 5,997,501 A | 12/1999 | Gross et al. |
| 6,027,459 A | 2/2000 | Shain et al. |
| 6,048,337 A | 4/2000 | Svedman |
| 6,050,988 A | 4/2000 | Zuck |
| 6,056,716 A | 5/2000 | D'Antonio et al. |
| 6,083,196 A | 7/2000 | Trautman et al. |
| 6,090,790 A | 7/2000 | Eriksson |
| 6,117,155 A | 9/2000 | Lee |
| 6,123,684 A | 9/2000 | Deboer et al. |
| 6,126,629 A | 10/2000 | Perkins |
| 6,132,449 A | 10/2000 | Lum et al. |
| 6,138,044 A | 10/2000 | Svedman |
| 6,144,869 A | 11/2000 | Berner et al. |
| 6,148,232 A | 11/2000 | Avrahami |
| 6,183,434 B1 | 2/2001 | Eppstein |
| 6,187,210 B1 | 2/2001 | Lebouitz et al. |
| 6,230,051 B1 * | 5/2001 | Cormier et al. ............... 604/20 |
| 6,233,471 B1 | 5/2001 | Berner et al. |
| 6,246,904 B1 | 6/2001 | Murdock |
| 6,254,580 B1 | 7/2001 | Svedman |
| 6,256,533 B1 | 7/2001 | Yuzhakov et al. |
| 6,317,630 B1 | 11/2001 | Gross et al. |
| 6,319,230 B1 | 11/2001 | Palasis et al. |
| 6,375,624 B1 | 4/2002 | Uber, III et al. |
| 6,408,204 B1 | 6/2002 | Hirschman |
| 6,440,096 B1 | 8/2002 | Lastovich et al. |
| 6,565,532 B1 | 5/2003 | Yuzhakov et al. |
| 6,611,707 B1 | 8/2003 | Prausnitz et al. |
| 6,678,556 B1 | 1/2004 | Nolan et al. |
| 6,743,211 B1 * | 6/2004 | Prausnitz et al. ........... 604/239 |
| 6,835,193 B2 | 12/2004 | Epstein et al. |

FOREIGN PATENT DOCUMENTS

| | | |
|---|---|---|
| EP | 302278 A1 | 2/1989 |
| FR | 757501 | 12/1933 |
| GB | 912194 | 12/1962 |
| GB | 2 335 990 | 10/1999 |
| WO | WO 93/17754 | 9/1993 |
| WO | WO 94/23777 | 10/1994 |
| WO | WO 95/07722 | 3/1995 |
| WO | WO 96/14026 | 5/1996 |
| WO | WO 96/37155 | 11/1996 |
| WO | WO 96/37256 | 11/1996 |
| WO | WO 97/48440 | 12/1997 |
| WO | WO 97/48442 | 12/1997 |
| WO | WO 99/62576 | 12/1999 |
| WO | WO 99/64580 | 12/1999 |
| WO | WO 00/05166 | 2/2000 |
| WO | WO 00/05339 | 2/2000 |
| WO | WO 00/16833 | 3/2000 |
| WO | WO 00/27473 | 5/2000 |
| WO | WO 00/67647 | 11/2000 |
| WO | WO 00/74763 A2 | 12/2000 |
| WO | WO 00/74765 A1 | 12/2000 |
| WO | WO 00/74766 A1 | 12/2000 |
| WO | WO 00/78212 A1 | 12/2000 |
| WO | WO 01/79706 A2 | 10/2001 |
| WO | WO 02/055128 A2 | 7/2002 |
| WO | WO 02/100469 A2 | 12/2002 |

* cited by examiner

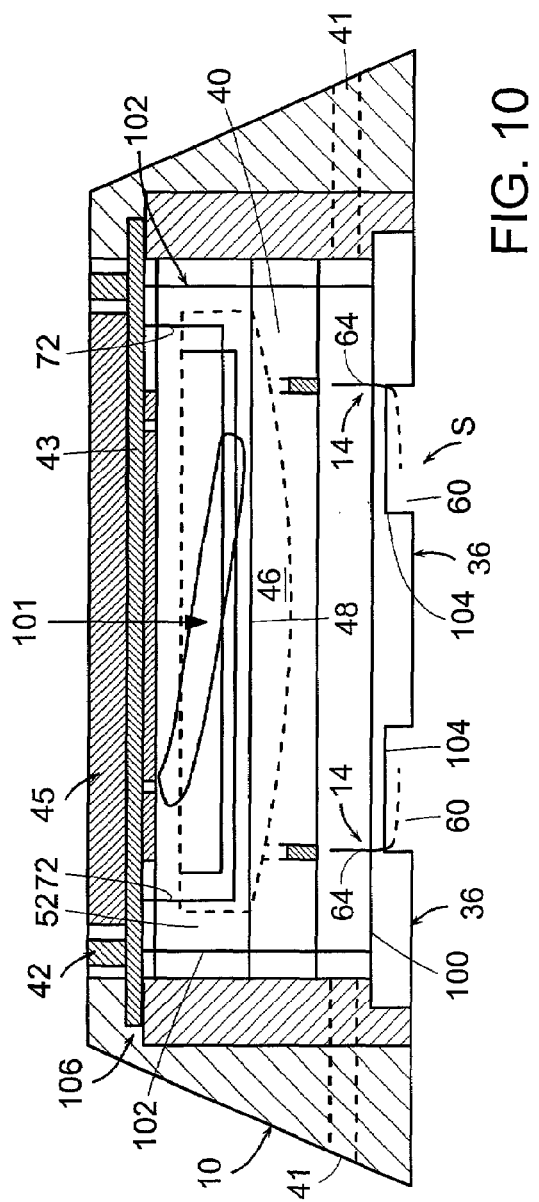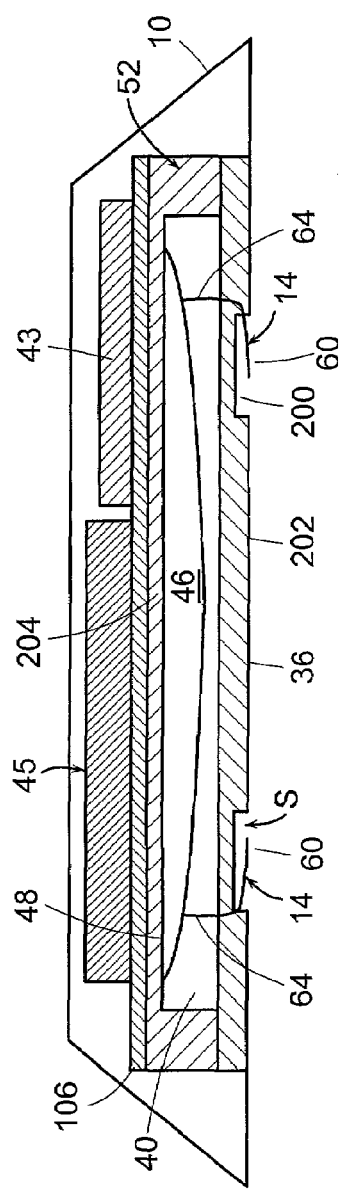

MICRONEEDLE TRANSDERMAL TRANSPORT DEVICE

RELATED APPLICATIONS

This application claims the benefit of U.S. Provisional Application No. 60/338,425, filed Oct. 26, 2001, and U.S. Provisional Application No. 60/399,489, filed Jul. 29, 2002.

The entire contents of the above applications are incorporated herein by reference.

BACKGROUND

Delivery of drugs to a patient is performed in a number of ways. For example, intravenous delivery is by injection directly into a blood vessel; intraperitoneal delivery is by injection into the peritoneum; subcutaneous delivery is under the skin; intramuscular is into a muscle; and orally is through the mouth. One of the easiest methods for drug delivery, and for collection of body fluids, is through the skin.

Skin is the outermost protective layer of the body. It is composed of the epidermis, including the stratum corneum, the stratum granulosum, the stratum spinosum, and the stratum basale, and the dermis, containing, among other things, the capillary layer. The stratum corneum is a tough, scaly layer made of dead cell tissue. It extends around 10-20 microns from the skin surface and has no blood supply. Because of the density of this layer of cells, moving compounds across the skin, either into or out of the body, can be very difficult.

The current technology for delivering local pharmaceuticals through the skin includes both methods that use needles or other skin piercing devices and methods that do not use such devices. Those methods that do not use needles typically involve: (a) topical applications, (b) iontophoresis, (c) electroporation, (d) laser perforation or alteration, (e) carriers or vehicles, which are compounds that modify the chemical properties of either the stratum corneum and/or the pharmaceutical, (f) physical pretreatment of the skin, such as abrasion of the stratum corneum (e.g. repeatedly applying and removing adhesive tape), and (g) sonophoresis, which involves modifying the barrier function of stratum corneum by ultrasound.

Topical applications, such as a patch, or direct application of a pharmaceutical to the skin, depend on diffusion or absorption through the skin. These methods of transdermal transport are not widely useful because of the limited permeability of the stratum corneum. Although techniques such as those listed above have been developed to enhance the effectiveness of topical applications, topical applications still cannot provide optimum transdermal transport.

On the other hand, invasive procedures, such as use of needles or lances, effectively overcome the barrier function of the stratum corneum. However, these methods suffer from several major disadvantages: pain, local skin damage, bleeding, and risk of infection at the injection site, and creation of contaminated needles or lances that must be disposed of. These methods also usually require a trained administrator and are not suitable for repeated, long-term, or controlled use.

Additionally, drug delivery through the skin has been relatively imprecise in both location and dosage of the pharmaceutical. Some of the problems include movement of the patient during administration, delivery of incomplete dosages, difficulties in administering more than one pharmaceutical at the same time, and difficulties in delivering a pharmaceutical to the appropriate part of the skin. Drugs have traditionally been diluted to enable handling of the proper dosages. This dilution step can cause storage as well as delivery problems. Thus, it would be advantageous to be able to use small, precise volumes of pharmaceuticals for quick, as well as long-term, delivery through the skin.

SUMMARY

The present invention implements an effective, multi-application microneendle transport system, which provides painless, precision insertion and controlled, programmable transport at commercially viable costs.

The microneedle transport device includes, at its most basic level, one or more microneedles connected to at least one reservoir. The microneedles can be provided in one or more rows or arrays. The arrays can be arranged in a Cartesian or circular pattern. A system for delivering substances to or withdrawing fluids from a patient can further include one or more actuators, pumps, and/or sensors. These elements can be combined in a variety of ways to produce systems with different attributes for delivery and/or collection of substances or information through the skin.

The microneedle transport device disclosed herein may have several applications, including but not limited to drug delivery, sampling, and biological monitoring. In application as a drug delivery device, each reservoir is filled with one or more drugs to be delivered. In sampling, each reservoir is initially empty and then filled with biological material, such as interstitial fluid. In monitoring, the device is adapted with sensors to monitor, for example, the concentration of a compound, such as glucose, in fluid that has been withdrawn, or with some receptor on the needle going into the skin (i.e., the fluid doesn't have to be withdrawn necessarily).

In one embodiment, the device includes a reservoir for holding a formulation of an active principle, and a needle with a bore extending along the length of the needle from a first end of the needle to a second end of the needle that is substantially aligned to a plane parallel to a body surface of a biological body when the device is placed on the body surface. The device also includes an actuator which pumps the formulation through the bore of the needle between a target area of the body and the reservoir. The device can include one or more additional needles like the needle described above, thereby forming an array of needles. In particular embodiments, the actuator moves the first end into the reservoir so that the bore is in fluid communication with the reservoir.

In certain embodiments, the second end of the needle moves in the plane to pierce the body surface. The actuator can pump the formulation into the biological body, and/or it can be reversible to draw the formulation into the vial. The needle can be positioned in a retracted state when the actuator is de-energized. A rotary actuator can be used to move the second end of the needle in the plane.

The actuator can include a vapor generator, or alternatively, the actuator operates by an electrochemical process, or is a conductive polymer.

In some embodiments, the device includes an oscillator which causes the second end of the needle to vibrate along its length to reduce the force required to drive the needle into the body. The oscillator can be a piezoelectric crystal which generates the vibration of the needles.

In certain embodiments, the device includes a sensor to monitor the status of a patient, for example, the glucose concentration of the patient. In such implementations, the formulation can be insulin pumped into the patient, with the amount of insulin pumped being based on the glucose concentration.

In another embodiment, the second end of the needle has tip end that is slanted and defines an opening from which the formulation is dispensed to control the direction of diffusion of the formulation into the body. The tip can be slanted between about 10° to 60°.

The second end of the needle can have a plurality of openings along its length such that the formulation is dispensed from and drawn through the plurality of openings. There can be one to 20 openings that are spaced apart between about 100 µm to 2 mm.

In yet other embodiments, the device includes a controller which directs the actuator to pump a desired amount of the formulation. The desired amount is dependent on input specifics of the body. The desired amount can be dispensed over a particular time period, lasting, for example, from 1 sec to 10 days. The desired amount of formulation can be dispensed incrementally over time. The body can be a human patient, such that the desired amount of the formulation is a sample collected from the patient drawn into the reservoir over a particular time period. The device can include a base unit that contains the needle, and a control unit that contains the controller. The base unit and the control unit can be separate connectable units.

Other embodiments are directed to methods of using the transdermal transport device described above.

Some embodiments of the invention may have one or more of the following advantages. The microneedle transport device disclosed here further presents the advantages of low manufacturing costs, and high efficiency. Particularly in regards to ease of use, the automated/mechanical system of the microneedle device reduces the error and uncertainty usually introduced by manual application. Very little (if any) pain, local damage, bleeding, or risk of infection is caused by the microneedles. Additionally, no special training or expertise is required to use the microneedle transport device. The device may further be adapted for disposable single-use, partial or full reuse, short or long-term use, or continuous or intermittent transport, or some combination thereof. The device is able to deliver a range of drug types and viscosities with variable delivery. For example, a significant amount of drug can be delivered in the beginning followed by maintenance dosing. The delivery can be periodic, for example, every hour, or can be on demand. The device provides for controllable and precise drug delivery to a location below the outer surface of the skin of the patient. That is, any desirable delivery profile can be set, for example, constant or intermittent, for delivery to a desired location. The device can provide on-demand delivery, for example, by pushing a button, when a patient desires some sort of pain control.

Since a precise amount of volume of drug can be delivered, there is a low volume of wasted drug. In addition to delivering a precise volume of drug with a variety of delivery profiles, the device is able to deliver a range of drugs. For example, the formulation may be a liquid, or a non-liquid that is reconstituted at delivery, or some combination thereof.

The device provides reduced pain as compared to traditional hypodermic injections, with minimal air injected under the skin. A user of the device is able to verify drug, dosing, expiration, etc. with, for example, a computer server via the internet. The impedance testing provides a convenient way of determining the depth of penetration of the needles. The device is small and portable, and the geometry of the device makes it comfortable to wear. The device is inexpensive and easy to use, and, hence, increases patient compliance. In addition, since the microneedles are protected within the base portion, exposure to contamination and/or accidental contact with a patient or medical clinician is eliminated or minimized.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 10 is a cross-sectional view of an alternative embodiment of the transdermal transport device.

FIG. 11 is a cross-sectional view of yet another alternative embodiment of the transdermal transport device.

DETAILED DESCRIPTION OF THE INVENTION

A description of preferred embodiments of the invention follows.

Figure 1:
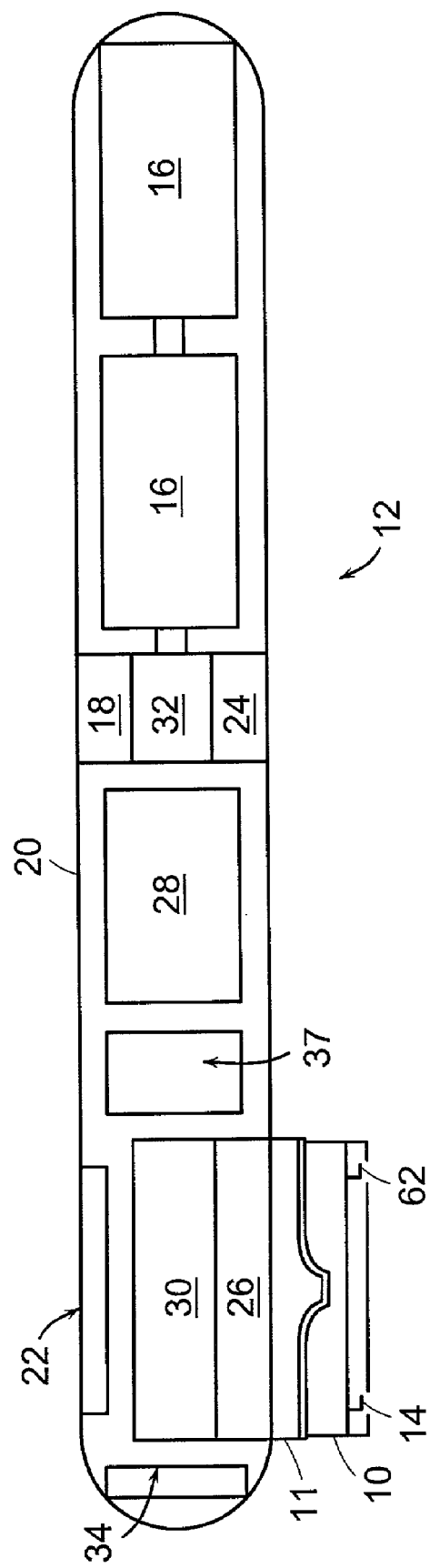
FIG. 1 is a side schematic view of an applicator with a transdermal transport device in accordance with the invention.

Referring to FIG. 1, there is shown a transdermal transport device 10 mounted to a coupling 11 of an applicator 12 which is used to attach the transport device 10 to the skin of a biological body, such as a human patient. Furthermore, the applicator 12 activates the device 10 to initiate the transport process before being disengaged from the device.

The device 10 includes an array of microneedles 14 for piercing the outer layers of skin of the patient and for delivering a formulation of an active principle such as pharmaceuticals through the skin to provide accurate delivery of the pharmaceuticals to the patient. Moreover, because of the shape and size of the needles and the minimal depth of penetration of the needles, contact between the needles and the nerve endings beneath the outer layer of the skin is minimized so that pain is reduced or absent in the patient. The pharmaceutical may be a liquid formulation, or it may be one or more non-liquid drugs that are reconstituted just before delivery.

The applicator 12 is powered by a set of batteries 16 and controlled by an embedded processor 18 positioned within a housing 20 which holds various other internal components of the applicator. A display 22, such as an LCD, mounted on top of the housing 20 communicates to a user the operating parameters of the transport device 10 and the applicator 12. The applicator 12 is able to communicate with a mother unit such as a PC and/or through the internet with a communication card 24. In some embodiments, the communication card is an ethernet card. Additionally or alternatively, the communication card can be a Bluetooth card which provides wireless communication capabilities.

The transport device 10 is mounted to the applicator 12 with an electromagnet 26. To disengage the transport device 10 from the applicator, voltage to the electromagnet is simply turned off to break the magnetic coupling between the top of the transport device 10 and the electromagnet 26. The applicator 12 also includes a vacuum pump 28 which draws a vacuum through a suction port 41 (FIG. 2A) to create a suction between suction ports 60 (FIG. 2A) of the transport device 10 and the skin of the patient to attach the device 10 to the skin. The microneedles 14 are bent at about a 90° angle about ⅓ of the distance from the tip 62 to the other end 64 (FIG. 2A) of each microneedle. Accordingly, as a rotary actuator 30, such as a stepper motor, shape memory alloy, contractile polymer, rotary solenoid, or any other suitable rotary actuator, rotates the transport device 10 and thus moves the mirconeedles 14, they penetrate laterally into the skin since the suction produced by the vacuum pump 28 also draws the skin into the suction ports 60 above a plane defined by the tip portions 62 of the microneedles. An impedance sensor 32 is used to indicate when the microneedles have sufficiently penetrated into the skin. A piezoelectric or a speaker 34 is also used to provide audible, perhaps verbal, indications to the user. The operation of the transport device 10 and applicator 12 will be described below in greater detail.

Figure 2A:
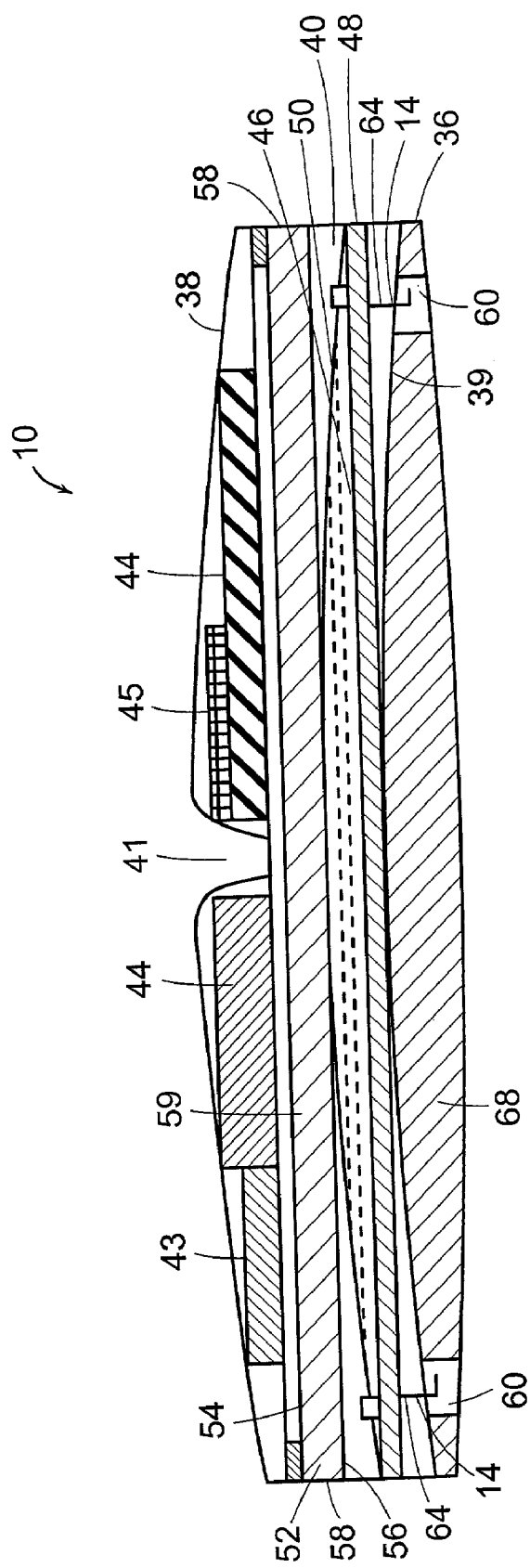
FIG. 2A is a cross-sectional view of the transdermal transport device shown in FIG. 1.
Figure 2B:
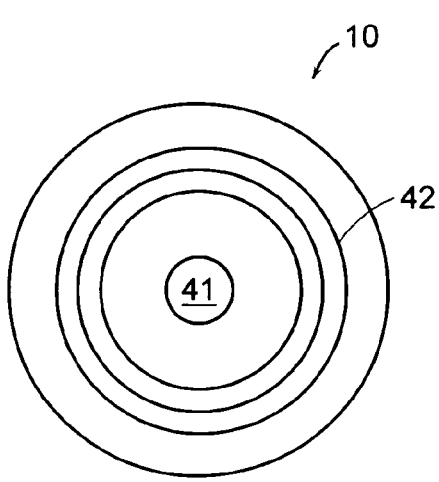
FIG. 2B is a top view of the transdermal transport device shown in FIG. 1.

Referring now to FIGS. 2A and 2B, in addition to a base portion 36 which holds the microneedles 14, the transport device 10 includes a control unit 38 and a drug vial 40. The control unit 38 is provided with electrical connections 42 which facilitate communication between the device 10 and the applicator 12, control electronics 43, and various sensors 44 that measure, for example, impedance, pressure, temperature, injection flow rate, as well as other sensors. Any of these sensors can also be located in the applicator 12, such as a pressure sensor 37. The control unit 38 also includes a power source 45 such as a supercapacitor and batteries which provide power to the device 10.

Figure 2C:
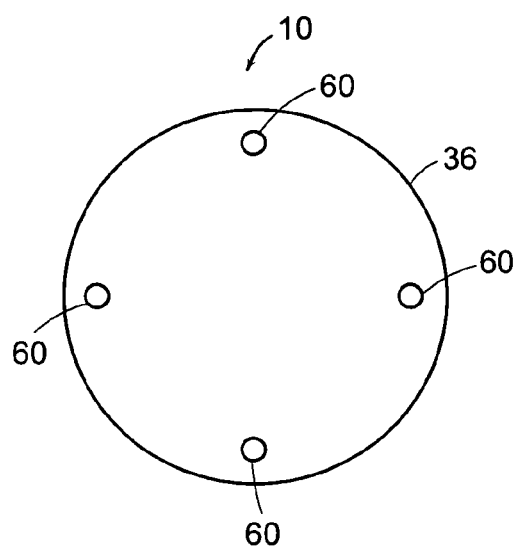
FIG. 2C is a bottom view of the transdermal transport device shown in FIG. 1.
Figure 2D:
FIG. 2D is a close-up view of a suction port shown in FIG. 2C illustrating a microneedle in retracted and protracted states.
Figure 2D:
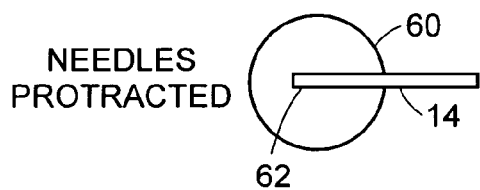

The drug vial 40 includes a drug chamber or reservoir 46 defined by a flexible membrane 48 and a rigid top section 50. Located above the drug vial 40 in the control unit 38 is an actuator 52. The actuator 52 is provided with a rigid base 54 that is joined to a cap 56 with a flexible bellow 58, or any other suitable expanding material, defining a chamber 59. As illustrated in FIGS. 2C and 2D, the suction ports 60 are located at the bottom of the base portion 36 to provide access for the tips 62 of the microneedles 14 to the skin.

In use, the applicator 12 is turned on by the user, such as a medical clinician, to activate the electromagnet 26 to attach the device 10 to the applicator 12. The user then delivers the device 10 to the skin. Next, the vacuum pump 28 creates a vacuum seal through the vacuum ports 60 with the skin to hold the device 10 in place, and also to make the skin more accessible to the microneedles 14 as discussed above.

Figure 3:
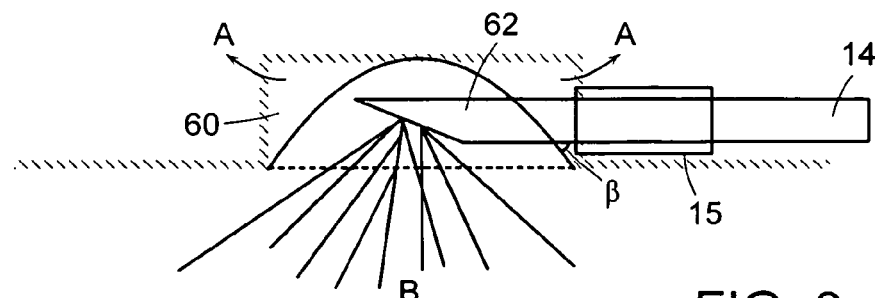
FIG. 3 is a close-up view of a tip of a microneedle of the transdermal transport device shown in FIG. 1 shown penetrating the skin of a patient and dispensing a drug into the patient.
Figure 4:
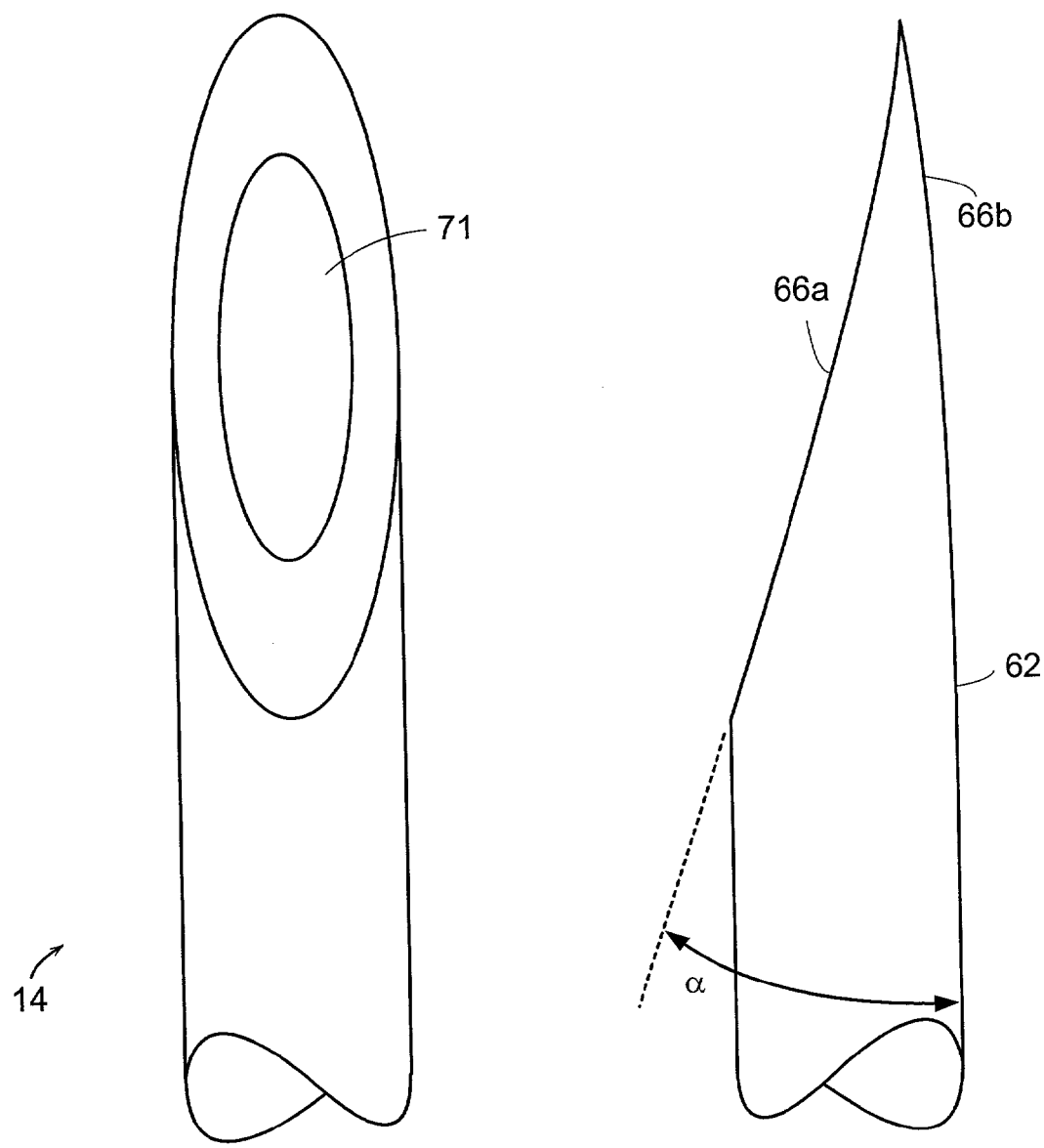
FIG. 4 is a close-up view of the tip of a microneedle of the transdermal transport device shown in FIG. 1.

Referring to FIG. 3, the vacuum pump 28 draws a suction, indicated by the arrows A, in the ports 60 to bring the skin up to the necessary height in the ports. The rotary actuator 30 then rotates and hence moves the microneedles 14 towards the skin in a direction at or about right angles to the direction of movement of the skin as it is sucked into the openings 60. Once the microneedles 14 contact the skin, they continue to move in the same direction approximately 50 μm to several mm into the skin, thereby penetrating the sidewall of the raised skin as illustrated in FIG. 4. In one embodiment, the penetration depth is approximately 200 μm. The extent of movement in this direction is dictated by the depth of the stratum corneum at the site where the microneedles 14 penetrate the skin. As stratum corneum depth varies, the applicator 12 uses the impedance sensor 32 to determine when the stratum corneum has been transversed. The impedance sensor 32 measures impedance of electric current flow between two of the microneedles 14. Impedance is high in the stratum corneum, and drops dramatically in the portion of the dermis just below the stratum corneum (see, e.g., FIG. 9B which shows a drop of approximately three orders of magnitude). The sensor 32 reads the change in impedance as the microneedles 14 penetrate into the skin, and movement is stopped when the impedance drops by an order of magnitude. Additionally or alternatively, there can be a hard mechanical stop, for example, the top of the ports 60, that prevents the microneedles from penetrating too deeply.

At this point, the vacuum pump 28 and the electromagnet 26 are de-activated to disengage the device 10 from the applicator 12. The vacuum seal between the device 10 and the skin is no longer needed to secure the device to the skin since the device 10 is now attached to the skin with the microneedles 14.

The control unit 38 of the device 10 then activates the actuator 52 which operates in the illustrated embodiment by an electrolytic process to cause the volume within the chamber 59 to increase and hence forcing the cap 56 against the rigid top section 50 of the drug vial 40, thereby pushing the drug vial 40 downwards. Consequently, the flexible membrane 48 is pushed against a bowed section 68 of a base plate 39, while the ends 64 of the microneedles 14 pierce through the membrane 48 and into the reservoir 46. Compression of the membrane 48 into the reservoir 46 expels the pharmaceutical through hollow pathways or bores of the microneedles into the skin. Thus, the device is able to deliver a pharmaceutical to a precise location just below the stratum corneum of the skin, as indicated by the letter B in FIG. 3.

Once the correct dose of the pharmaceutical is delivered, the device 10 is reattached to the applicator 12 and the rotary actuator 30 moves the microneedles out of the skin to disengage the device 10 from the patient. Typically, the base portion 36 and the drug vial 40 are discarded, while the control unit 38 is re-used. The device 10 is used to deliver precise amounts of drugs as needed by a patient. Information relating to the patient can be relayed through an associated computer to the device 10 and the applicator 12 via the communication card 24.

The same device 10 can be used for collecting fluid, such as interstitial fluid, from the dermis. For collection to occur, the reservoir 46 must first be compressed. This is accomplished by moving the drug vial 40 downward with the actuator 50 such that the membrane 48 of the reservoir 46 is compressed to expel any air in the reservoir 46. Upon penetration of the microneedles into the skin, the expansion chamber 59 of the actuator 52 is contracted to allow the drug vial 40 to rise which creates a vacuum inside the reservoir 46 to draw fluid through the microneedles into the reservoir 46.

Thus, the actuator 52 acts as a pump which facilitates pumping a drug through the microneedles into the skin or collecting a sample from the patient. The actuator 52 can be used to create a vacuum within the reservoir 46 before the device 10 is placed against the skin. In sum, the actuator 52 provides controlled, programmable transport to and from the target site.

The various features of the transport device 10 and the applicator 12 will now be described in greater detail.

In the present application, the term "microneedle" is intended to be construed as singular or plural, unless specifically modified by a term indicating the number of microneedles. Microneedles disclosed herein may be porous or non-porous, uniform or of varying diameters or cross-sectional geometries, or some combination thereof. Hollow microneedles with uniform diameter are sometimes referred to as microtubes. As used herein, the term "microneedle" refers to both microtubes and any other kind of microneedle as described previously. Additionally, microneedles may also have openings at either or both ends, as well as, on the side-walls at various and/or multiple positions along the length, or any combination thereof. Further, either or both ends of the microneedle may be flat, tapered to a point, rounded, or beveled from one or more sides, as described below.

As shown in FIG. 4, the tip 62 has an opening 71 and is cut at an angle, α, of approximately 10° to 60°, to provide a slanted surface 66a. This surface 66a and/or the outer surface 66b can be beveled. The illustrated embodiment has four microneedles 14, but there can be ten microneedles or more. The microneedles 14 are metal welded or soldered to the base plate 39, made from, for example, stainless steel, of the base portion 36, and the bellows 58 is formed of a polymer and is ultrasonic welded to the base 54 and the cap 56 of the actuator 52, or the bellow can be permanently attached to either the control unit 38 or the drug vial 40. Alternatively, these parts may be fitted together via a thermal seal or any other suitable technique for forming a fluid-tight seal. Note that the device 10 is in use or not, the microneedles 14 are always contained within the base portion 36 and never extend outside of the suction ports 60 beyond the bottom of the base portion 36. This minimizes or eliminates contamination of the microneedles and accidental contact between the needles and a patient or medical clinician.

The beveled surfaces 66a and/or 66b of the tip 62 has many advantages. It reduces the trauma to the skin; it further reduces any pain felt by the subject; it prevents coring of the tissue into the microneedle; and it decreases the amount of force required for penetration into the skin. Particularly, in regards to coring, sharp tipped microneedles having a small inner diameter are less likely to accumulate tissue within the hollow opening, thereby avoiding transport blockage. In the above embodiment, both ends of each microneedle 14 are sharpened: one end for insertion into the skin, and the other end for insertion through membrane 48 into the reservoir 46.

Figure 5:
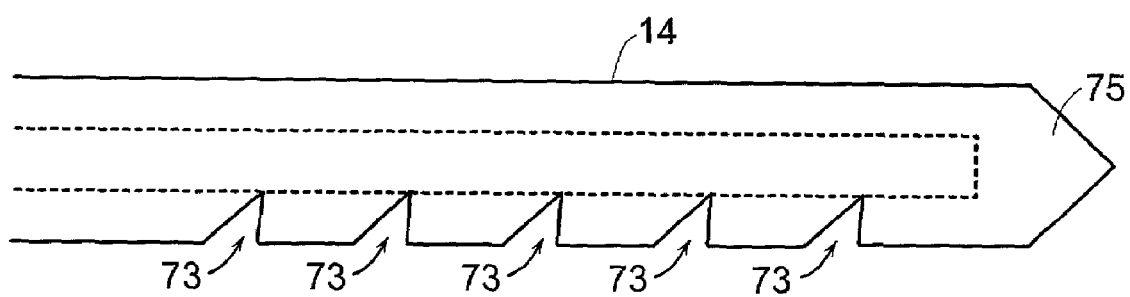
FIG. 5 is a side view of an alternative embodiment of a microneedle in accordance with the invention.

In certain embodiments, as illustrated in FIG. 5, the microneedles 14 can have holes 73 on the side-walls at various and/or multiple positions along the length through which fluid can be transmitted, combined with the openings 71 (FIG. 4) or with solid tips 75. There can be from one to 20 or more holes 73. The spacing between the holes is approximately in the range of 100 μm to 2 mm.

The microneedles 14 may be manufactured from a variety of materials and by a variety of methods. Representative materials include metals, ceramics, semiconductors, organics, biodegradable and non-biodegradable polymers, glass, quartz, and various composites. Representative methods include micro-fabrication techniques. In the above illustrated embodiment, the microneedles 14 are made of medical grade stainless steel, such as 304 stainless steel. Stainless steel microneedles are advantageous because they are durable, semi-flexible, and have the mechanical strength to endure insertion into the stratum corneum. They can be cut from readily available, relatively inexpensive commercial stock via a chemical saw, or any suitable technique, to the desired dimensions, and ground to the desired tip geometry.

The microneedles 14 have an inner diameter of about 10 μm to 100 μm, an outer diameter of 30 μm to 250 μm, and a length of approximately 5 mm to 10 mm. In the above illustrated embodiment, each of the microneedles has an inner diameter of 54 μm, and an outer diameter of 108 μm. Other embodiments use microneedles with an inner diameter of about 100 μm and outer diameter of about 175 μm.

The microneedles 14 can also be coated on the outside, the inside, or both. Coatings can cover part or all of either or both surfaces. Coatings can be selected from, but are not limited to, the group consisting of lubricants, chemical or biological reaction elements, and preservatives.

The microneedles may be made of one or more rows of microneedles of uniform or varying dimensions and geometries, with uniform or varying spacing, at uniform or varying projection angles, and any combination thereof. In the embodiment above, the set of microneedles form a circular array of four microneedles. The array has a radius of approximately 5 mm to 20 mm. In the illustrated embodiment, the radius is about 12 mm. In another embodiment, the set may include more than one circular array of microneedles. In yet another embodiment, the microneedles are arranged in an X by Y array, where X may or may not equal Y.

Additionally, as described above, the microneedle is bent, at approximately a 90° angle. As shown in FIG. 3, the bend of around 90° is positioned such that the segment from the bend to the tip 62 of the microneedle is long enough to penetrate through the stratum corneum. However, the angle, curvature, and location of the bend in the microneedle, as well as the orientation of the microneedle with respect to the device 10, can vary. For example, the bend angle may be 90° or more or less, but typically less than 180°.

In the bent microneedle embodiment, the bevel side 66a faces away from the bend and towards the skin surface, prior to insertion of the microneedle into the skin, and continues to face away from the rest of the device once it is inserted. Penetration occurs at "acute-angle insertion" of the microneedle. The angle of insertion, p, (FIG. 3) is the angle formed by the skin surface and the microneedle 14, with the vertex of the angle at the point of contact between the microneedle and the skin surface. Acute-angle insertion reduces the associated pain relative to 90° insertion. The microneedle, with varying bend angle, can be oriented for an insertion angle from 0° to 90°. Where the microneedle is close to or perpendicular to the skin at the entry site, a clear pathway for the substance to exit the skin is created upon withdrawal of the microneedle, resulting in leakage. Delivery of a complete dose of a substance under the stratum corneum is improved by the low acute angle insertion, especially when coupled with the downward facing beveled tip. The substance will more readily move down through the dermis. Moreover, with a low acute angle insertion, one has better control of the needle insertion depth.

Figure 6A:
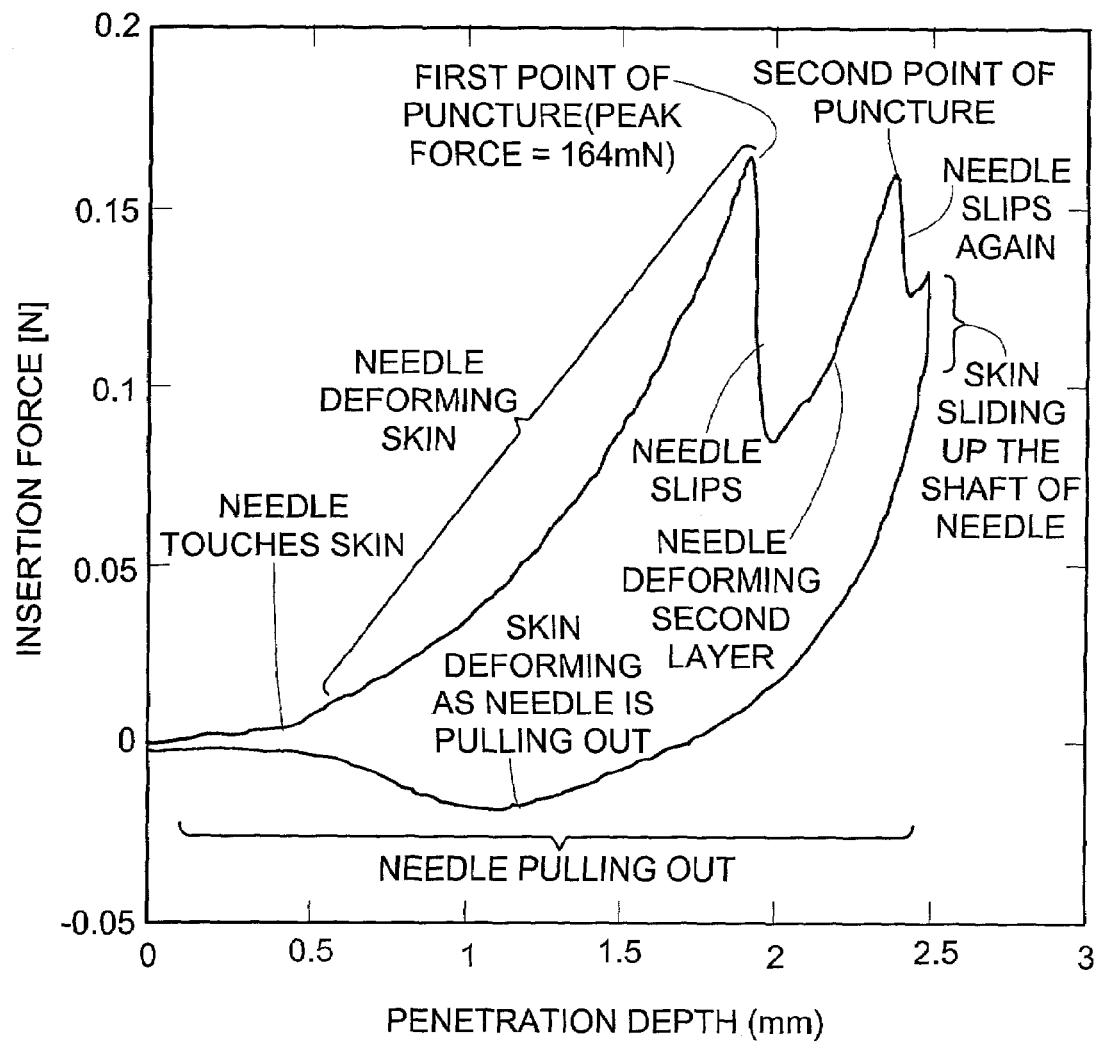
FIG. 6A is a graph of the insertion force of a microneedle versus the penetration depth of the microneedle.
Figure 6B:
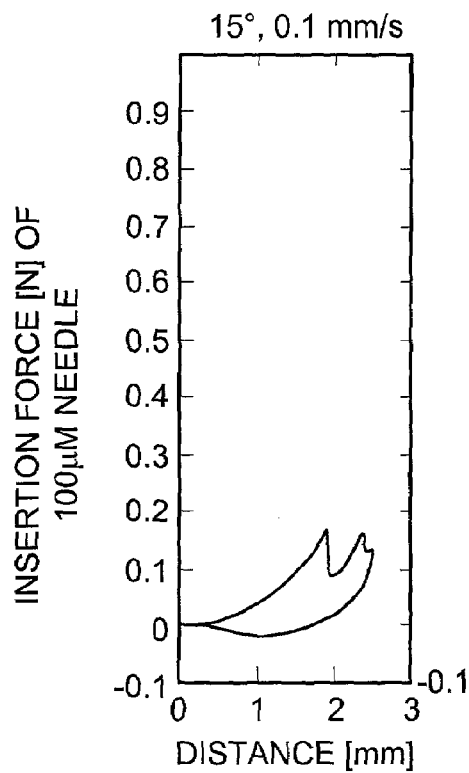
FIGS. 6B-6I is a sequence of graphs of the insertion force of a microneedle versus the penetration depth of the microneedle for different diameter needles.

Referring to FIG. 6A, there is shown a plot of insertion force of a needle versus penetration depth, illustrating the skin and needle behavior as described by the various labels. After the needle touches the skin, the skin is deformed until a first point of puncture, after which the needle slips. Subsequently, the needle deforms the second layer of skin until a second point of puncture, after which the needle slips again. Then the skin slides up the shaft of the needle. As the needle is pulled out, the skin is also deformed, as shown in the bottom portion of the graph.

Figure 6C:
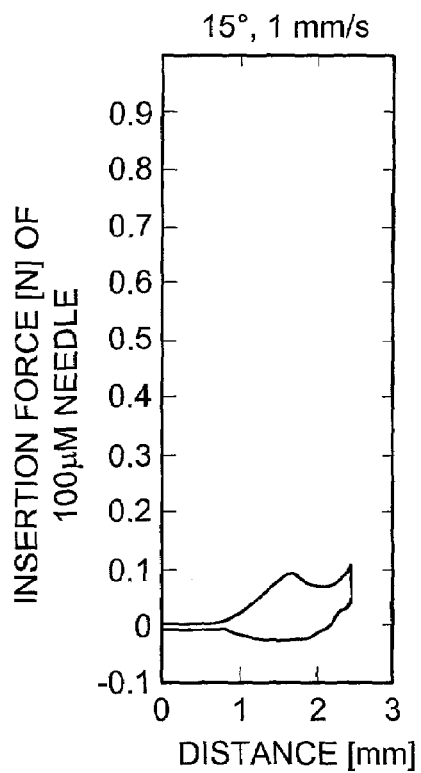
Figure 6D:
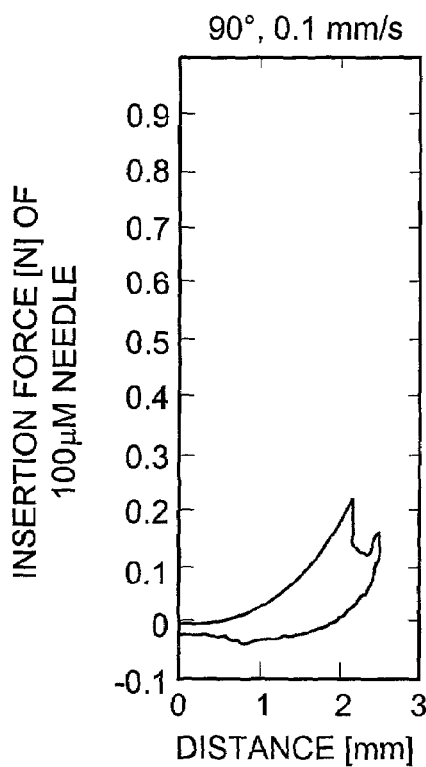
Figure 6E:
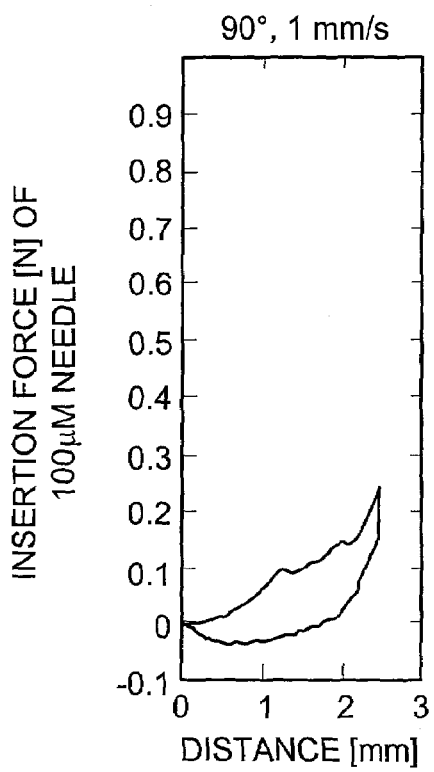
Figure 6F:
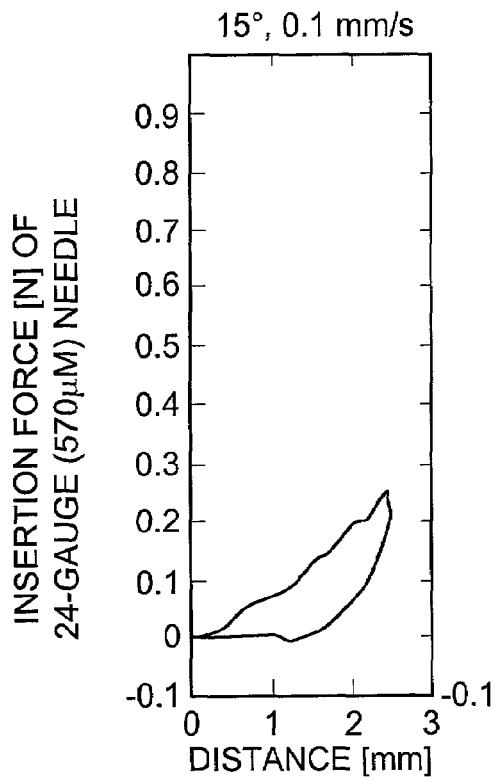
Figure 6G:
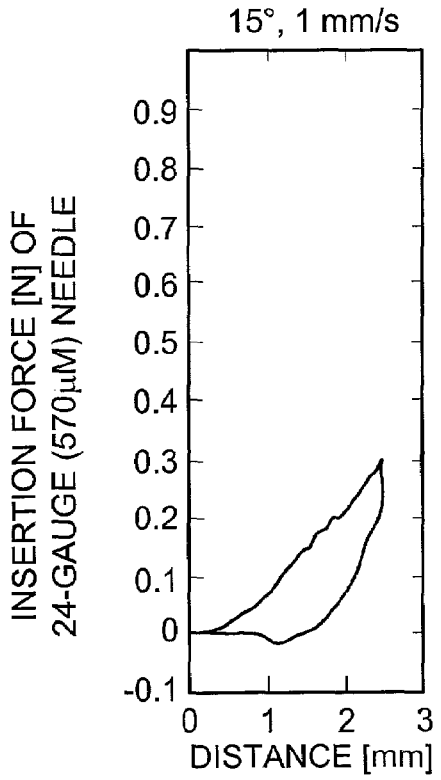
Figure 6H:
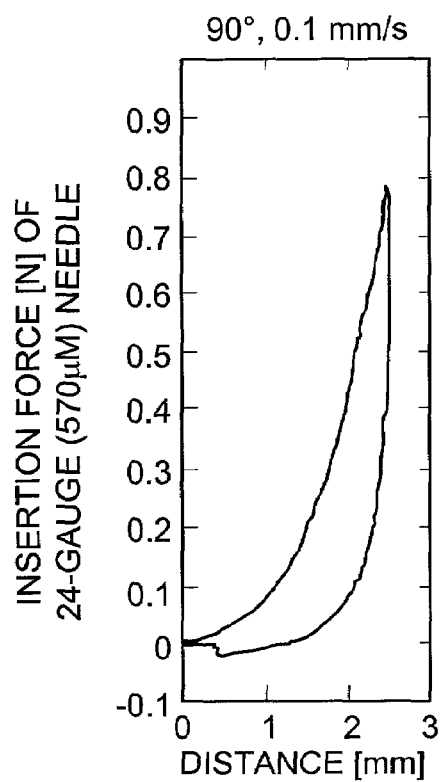
Figure 6I:
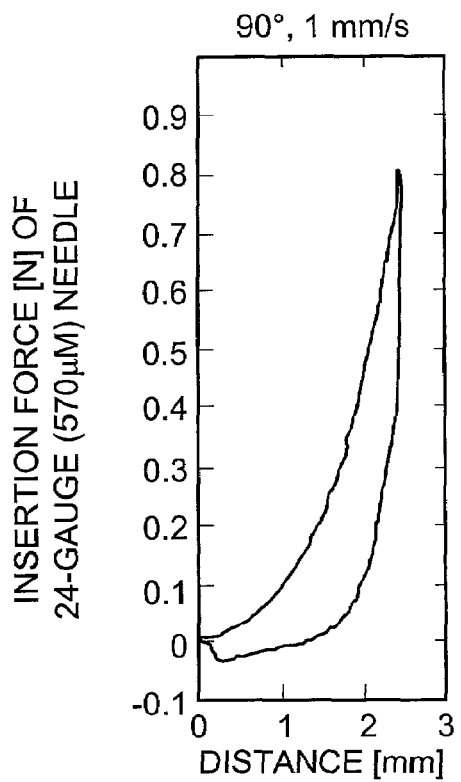

Turning now to FIGS. 6B-6I a sequence of graphs illustrate the insertion force [N] versus penetration depths [mm] profiles for 100 μm (top graphs, FIGS. 6B-6E) and 570 μm (bottom graphs, FIGS. 6F-6I) needles that are at an angle of 15° to 90° with respect to the surface of the skin and for needle insertion velocities of 0.1 and 1.0 mm/s. As is evident from the figures, the smaller needles have significantly smaller penetration forces. The figures also show that the velocity of needle insertion does not significantly affect the penetration forces. Finally, the figures show that needles inserted at smaller angles (for example, 15°) to the surface of the skin require smaller penetration forces. The peak insertion force for a 100 μm needle into the skin at a 90° angle at a velocity of 1 mm/s is approximately 250 mN (FIG. 6E), while the peak insertion force for a 100 μm needle into the skin at a 15° angle at a velocity of 1 mm/s is approximately 175 mN (FIG. 6C).

Thus, the microneedles 14 need not be parallel to the skin. They can be angled downward, for example, to facilitate penetration into the skin. The base 36 can be pushed against the skin so that portions of the skin will rise within access ports similar to the suction ports 60.

The rigid top section 50 of the reservoir 46 is made from stainless steel, glass, such as Type I or Type II high purity glass, or polymer, and the flexible membrane 48 is approximately 20 μm to 300 μm, preferably 100 μm, thick, and is made from a deformable elastopolymer such as silicone rubber or any other suitable flexible material. The reservoir 46 is typically filled with one or more pharmaceuticals for delivery to the patient, and then sealed.

In the embodiment shown in FIGS. 2A and 2B, the reservoir 46 is a single-chambered, hollow container with one rigid top section 50, and one deformable membrane 48. The reservoir 46 has a maximum fill thickness of approximately one to 5 mm, preferably about 2 mm, and a volume capacity approximately in the range of 100 μl to 5 ml In the device 10, the microneedles 14 are in contact with the pharmaceutical in the reservoir 46 when the ends 64 of the microneedles are inserted into the reservoir. There can be a semi-permeable membrane, filter, or valve placed between the reservoir 46 and the openings at the ends 64 of the microneedles. The membrane or filter can serve to purify the substance, or remove a selected material from the substance entering or leaving the reservoir. A membrane or filter can also contain a binding partner to the selected material, thereby capturing or trapping that material during the transport. The binding partner can be specific or nonspecific. A valve is useful in preventing leakage as well as in precisely releasing a set amount of substance. The valve is also useful to prevent backflow of a collected fluid through the microneedles. In some embodiments, a microvalve is opened in each microneedle 14 to allow movement of fluid for delivery or collection. For example, the microvalve could be embedded in the microneedles 14 or be part of the reservoir 46. Alternatively, a non-permeable membrane, covering for example the end of the microneedle opening into the reservoir, can be breached to allow the fluid movement.

Rather than being a hollow chamber, in some embodiments the reservoir 46 can be a porous matrix, single or multi-chambered, or any combination thereof. The reservoir 46 can contain one or more chambers. Each chamber can be the same or may differ from any or all of the others. For example, a reservoir 46 can have one chamber that contains a reagent and into which fluid is drawn through the microneedles. A reaction might then occur in this first chamber, the results of which might trigger manual or automatic release of a substance from the second chamber through the microneedles into the skin.

The reservoir 46 is easily loaded with a substance to be delivered. Loading can occur before or after association of the reservoir 46 with the microneedles 14. As mentioned earlier, the formulation can be one or more non-liquid drugs (for example, that have been dehydrated) that may be preloaded into the reservoir and then reconstituted before delivery. In some embodiments, the inside of the reservoir 46 is coated with a material prior to assembly of the reservoir. The coating can have one or more purposes, including, but not limited to, aiding flow so that the substance exiting or entering the reservoir moves smoothly and/or does not leave behind droplets, serving as a reactant used for detecting the presence or absence of a particular material in the fluid, and/or serving as a preservative.

When the transport device 10 is used to deliver drugs, the reservoir 46 stores one or more drugs in one or more chambers to be delivered to the target site. The reservoir 46 can be filled with the desired drug through an opening situated opposite the placement of the microneedles 14. Alternatively, the desired drug can be drawn up into the reservoir 46 through the microneedles or the desired drug can be placed within the reservoir 46 when it is sealed.

When the transport device 10 is used to obtain samples from the patient, the reservoir 46 stores, in one or more chambers, one or more biological samples drawn from the patient. The device can include one or more elements directed at securing the sample within the reservoir during removal of the device from the skin. These elements might include valves, flaps and the like.

Although in the embodiment illustrated in FIGS. 1 and 2 a vacuum seal is initially used to secure the device 10 to the skin, alternative mechanisms for securing the device 10 on the skin are available that include, but are not limited to, one or more straps, tape, glue, and/or bandages. The outer casings of the control unit 38, the drug vial 40, and the base portion 36 can be made of any stiff material, such as, but not limited to, stainless steel and other hard metals, plastics, woven or matted stiffened fibers, cardboard, and wood.

The actuator 52 disclosed herein facilitates pumping a drug through the microneedles into the skin or removing a sample from the patient. The actuator 52 can be used to create a vacuum within the reservoir 46 before the device 10 it is placed against the skin. The actuator 52 provides controlled, programmable transport to and from the target site.

In the illustrated embodiment, the actuator 52 operates by an electrochemical reaction, in particular electrolysis of water ($H_2O$) that converts water into hydrogen ($H_2$) and oxygen ($O_2$) gas. There are two electrochemical reactions taking place: oxidation is occurring at the anode according to the reaction $$2H_2O(l) \rightarrow O_2(g) + 4H^+(aq) + 4e^-$$

and reduction is occurring at the cathode according to the reaction $$2H_2O(l) + 2e^- \rightarrow H_2(g) + OH^-$$

To keep the numbers of electrons balance, the cathode reaction must take place twice as much as the anode reaction. Thus, if the cathode reaction is multiplied by two and the two reactions are added together, the total reaction becomes $$6H_2O(l) + 4e^- \rightarrow 2H_2(g) + O_2(g) + 4H^+(aq) + 4e^-$$

The $H^+$ and $OH^-$ form $H_2O$ and cancel species that appear on both side of the equation. The overall net reaction therefore becomes $$6H_2O(l) \rightarrow 2H_2(g) + O_2(g)$$

Hence, three molecules (1 $O_2$, 2 $H_2$) are produced per 4 electrons. That is, the number of moles of gas created by electrochemical decomposition of water as described by the following equation is $$n_{gc} = n_{ge}/(eN_A) = 7.784 \times 10^{-6} \, mol/C$$

where $n_{ge}$ is the number of molecules of gas produced per electron put into the system, ¾, e is the charge of one electron, and $N_A$ is Avogadro's number. This conversion results in a large volume change of over, for example, three orders of magnitude, which is harnessed to expel the drug from the reservoir 46. When the conversion of water to hydrogen and oxygen occurs, the expansion compresses the flexible membrane 48, expelling the drug and any carriers or other compounds or solvents out of the reservoir 46 through the microneedles 14.

Figure 7A:
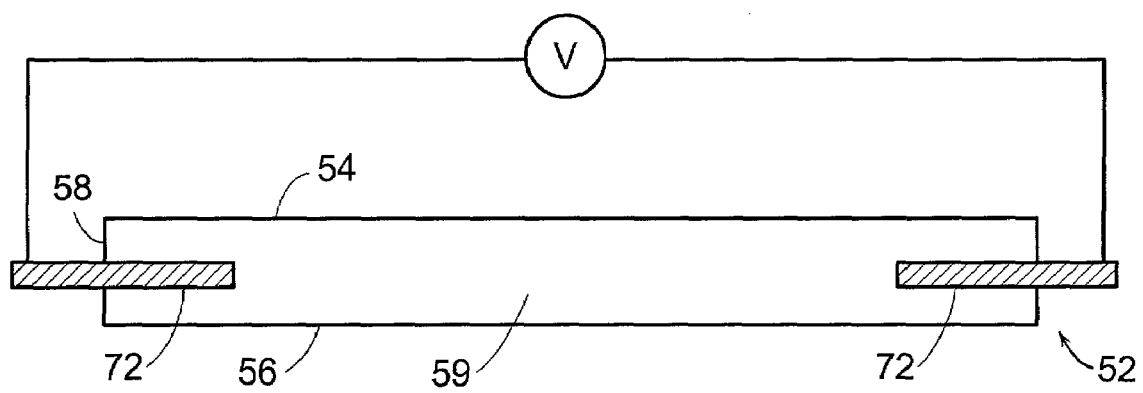
FIG. 7A is a view of an actuator of the transdermal transport device shown in FIG. 2A.

Referring in particular to FIG. 7A, there is shown the actuator 52 by itself for illustrative purposes. The chamber 59 contains, for example, 1 µl to 10 ml, preferably, 1 µl to 1 ml, of water with 1 M of $Na_2SO_4$ or NaOH. To initiate the electrolytic process, a current, I, is applied to two electrodes 72 positioned within the chamber 59 of the actuator 52. Each electrode 72 can be solid or a mesh. The mesh configuration provides a larger surface area to initiate the decomposition process. The electrodes can be made of stainless steel, platinum, or platinum/iridium gauze, such as Alfa Aesar #40934, or any other suitable material.

Figure 7B:
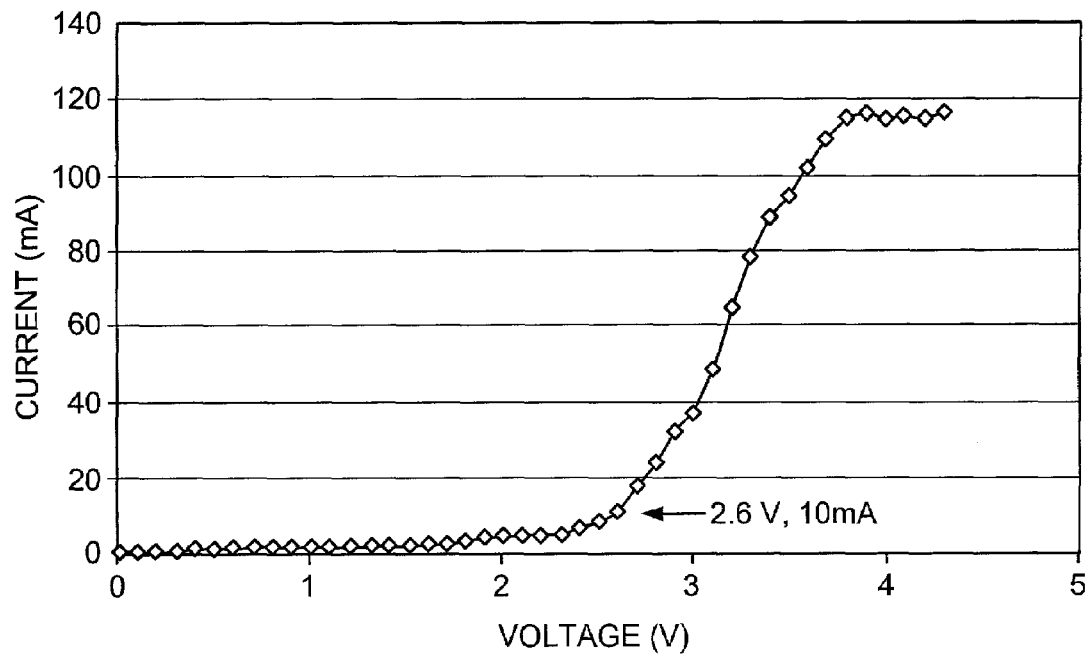
FIG. 7B is a graph of the voltage requirements of the actuator shown in FIG. 7A with stainless steel electrodes.
Figure 7C:
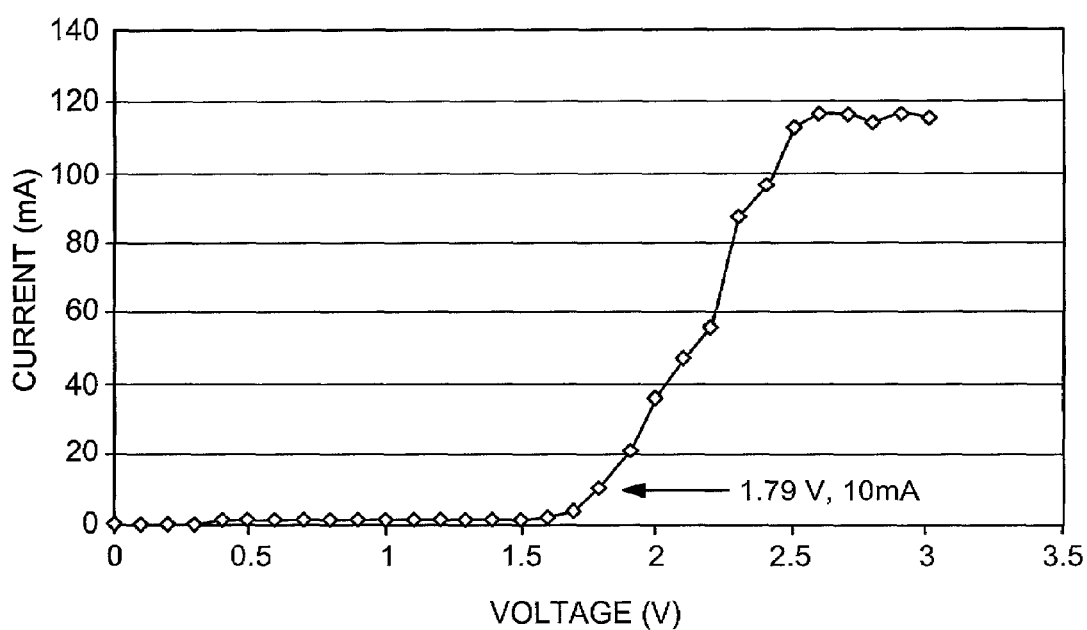
FIG. 7C is a graph of the voltage requirements of the actuator shown in FIG. 7A with Nichrome electrodes.

Referring to the graph depicted in FIG. 7B, there is shown a representative voltage to current relationship for the actuator or pump 52 with two 3 mm×12 mm×50 µm thick stainless steel electrodes. FIG. 7C shows the voltage to current relationship for the actuator 52 with two 40 mm long Nichrome electrodes. Both FIGS. 7B and 7C show that no current is drawn, and therefore no gas is created, until the voltage reaches approximately 1.7 V. At this point, the current drawn by the pump begins to increase almost linearly until the current reaches approximately 115 mA, where it reaches steady state. The current versus voltage slopes for the linear region are different based on the electrode materials and configuration. For the pump 52 with stainless steel electrodes (FIG. 7B), the pump reaches steady current consumption at approximately 3.8 V, while the pump with Nichrome electrodes (FIG. 7C) reaches steady current consumption at approximately 2.5 V. Furthermore, at an operating current of about 10 mA, the operating voltage is about 2.5 V and 1.79V for the stainless steel electrodes, and the Nichrome electrodes, respectively. The electrolytic process can be easily stopped and if desired initiated again, and this process can be repeated to precisely control the expansion rate of the chamber 59 and hence the drug delivery rate of the device 10.

The actuator 52 can be a micro-electric motor, such as, for example, Lorentz force or electrostatic motors, or operate by chemical or electrochemical reactions, contractile polymers, shape memory alloys, or any other suitable mechanism to facilitate the transport of the pharmaceutical. Alternatively or additionally, the actuator can include mechanical or organic members, such as micro-valves or permeable membranes, respectively, to further control transport rates. The actuator 52 can also be any other suitable micro-mechanism, such as motors, levers, pistons, solenoids, magnetic actuators, and the like, for controlling the motion of the flexible membrane 48 of the drug vial 40 to provide precise and controlled delivery of compounds and/or collection of body fluids.

In certain embodiments, the actuator 52 operates as a vapor generator. Liquid water, for example, contained in the chamber 59 of the actuator 52 is heated with an onboard heater which causes the liquid to change to steam resulting in a significant increase in volume. In such embodiments, the volume of the liquid water is about 500 nl to 5 µl. The temperature of vaporization of water is 100° C., and at that temperature the latent heat of vaporization is 2.25 kJ/kg. Thus for 1 µl of liquid water, the steam volume becomes approximately 1.706 ml.

Alternatively, the top section 50 of the reservoir 46 can be formed from a conducting polymer, such as polypyrrol, which contracts (usually in one direction) under the application of a low voltage current. The conducting polymers act like human muscle, that is, they contract lengthwise. The force produced per area of these polymers is about 1 to 10 Mpa, which is about a factor of 10 greater than that of human muscles. The change in length of these polymers is about 2%. Contraction of the conducting polymer forces the drug and any carriers or other compounds or solvents out of the reservoir 46.

When the device is used to collect samples, the actuator 52 functions as a reversible actuator to facilitate transport from the target area to the reservoir 46. For example, in the conducting polymer pump system, initial application of a low voltage current compresses the top section 50, emptying the reservoir 46. While the reservoir is in its contracted state, the device 10 is applied to the target site. The voltage is then disrupted to allow the polymer to expand to its natural state. Expansion of the reservoir 46 creates a vacuum inside the reservoir, which causes fluid to be drawn into the reservoir.

Another embodiment of the actuator 52 is a shape memory alloy or contractile polymer wrapped around a circle. The actuator forms a twist that is guided along a thread so that there is a linear (vertical) motion which places a force on the drug vial 40, thereby expelling the drug from the reservoir 46. The actuator is returned to its initial retracted state by one of many available means that includes but is not limited to shape memory alloys, springs, and super-elastic metal.

Recall, the vacuum pump 28 of the applicator 12 creates a suction to draw the skin in one direction into the openings 60 of the transport device 10, and the rotary actuator 30 provides an orthogonal direction of motion of the microneedles 14 to facilitate acute-angle insertion into the skin with the bent microneedles 14.

In other embodiments, these orthogonal motions may be accomplished by use of one or more actuators. For example, an actuator can be used to move the microneedles in a direction perpendicular to the skin surface so that the bent portion of the microneedle are parallel to and come into contact with the skin, with the microneedle tip opening facing the skin. The actuator continues to move the microneedles in the perpendicular direction, causing them to depress the skin under the microneedle, and resulting in the neighboring skin being above the level of the microneedle tips. The rotary actuator 30 then moves the microneedles 14 forward in the direction of the microneedle tip 62, parallel to the skin surface. The microneedle tips 62 contact the surface of the skin at the side of the depression formed by the initial perpendicular motion of the microneedle. The rotary actuator 30 continues to move the microneedles in the parallel direction causing the microneedles to penetrate the stratum corneum. When the microneedle tip 62 has reached the target site, the rotary actuator stops the motion. One or more actuators can be involved in each motion. Again, a stop signal can be generated using the impedance sensor system 32, discussed in detail below. Alternatively, there can be a hard mechanical stop or the insertion motion can be stopped after a defined distance of penetration, or a defined period of time of insertion. Removal of the microneedles 14 is accomplished in basically the reverse order.

Any of the foregoing embodiments, as well as any other applicable to the situation, could be synchronized with the impedance sensor 32, discussed in detail below, so that the drop in impedance, upon penetration through the stratum corneum, triggers the pumping action of the actuator 52, such as the electrolytic, chemical reaction, polymer contraction actuators, or an electric motor or any other actuators used in the device 10.

In certain embodiments, the device 10 is provided with contoured, drilled tunnels or tunnels or guide sleeves 15 through which the microneedles 14 are guided into the skin.

For safety and other reasons, the microneedles 14 can have caps or holsters covering the tips 62, as discussed previously, requiring additional movement of the device 10 as a first step to uncap the microneedles 14. The caps can be fastened to a moveable part within the device 10, and this part is moved by an actuator away from the microneedle tips to uncap the stationary microneedles 14. In another embodiment, the caps may be a free-standing structure that is manually removable prior to application, or the microneedles may penetrate through the protective caps prior to application.

In some embodiments, the transport device 10 and/or the applicator 12 is combined with an oscillator system, made from, for example, a piezoelectric crystal, to assist the insertion of the microneedles 14. The oscillator system can be an independent system, integrated with the actuators, or some combination thereof. Preferably, the microneedles are vibrated at 10 kHz in the direction of the penetration motion. A potential advantage of using such an oscillator system is that less force may be required to penetrate the skin.

As discussed above, the device 10 includes electrical sensors, such as the impedance sensor 32 which detects penetration of the stratum corneum. That is, the sensor 32 signals when the desired insertion of the microneedles 12 have been achieved. The determination of the location of the microneedle tip(s) within or through the stratum corneum allows for delivery of a complete, predetermined dose to the patient at a location amenable for absorption by the patient's body.

This is accomplished by measuring impedance of the tissue as the microneedles proceed through it. As the stratum corneum creates a high level of impedance, and the tissue beyond the stratum corneum only provides a relatively low level of impedance, impedance is monitored to determine when the microneedles have passed through the stratum corneum. At that point insertion may be stopped so as to avoid penetrating the skin layer containing nerves and capillaries.

Figure 8A:
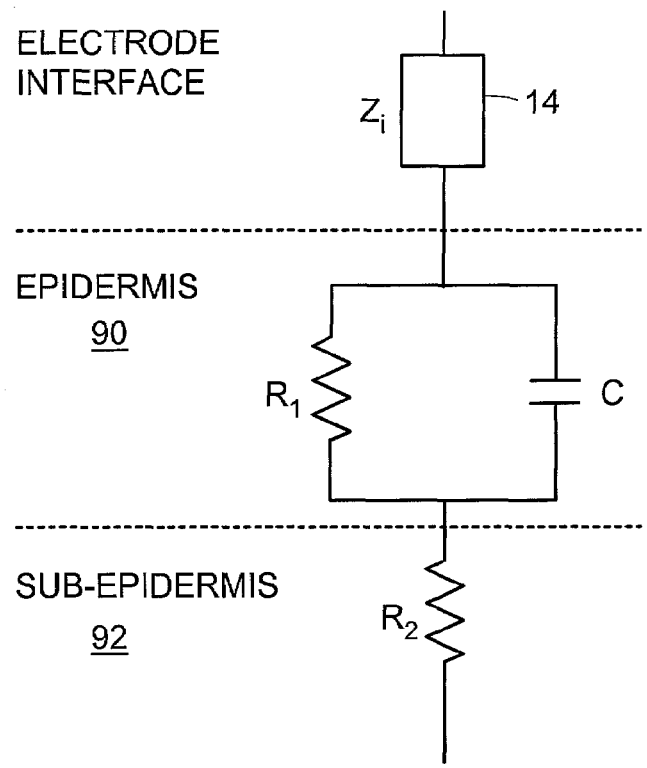
FIG. 8A is schematic of a circuit formed with electrodes of an impedance sensor of the transdermal transport device shown in FIG. 1 and the skin of a patient.
Figure 8B:
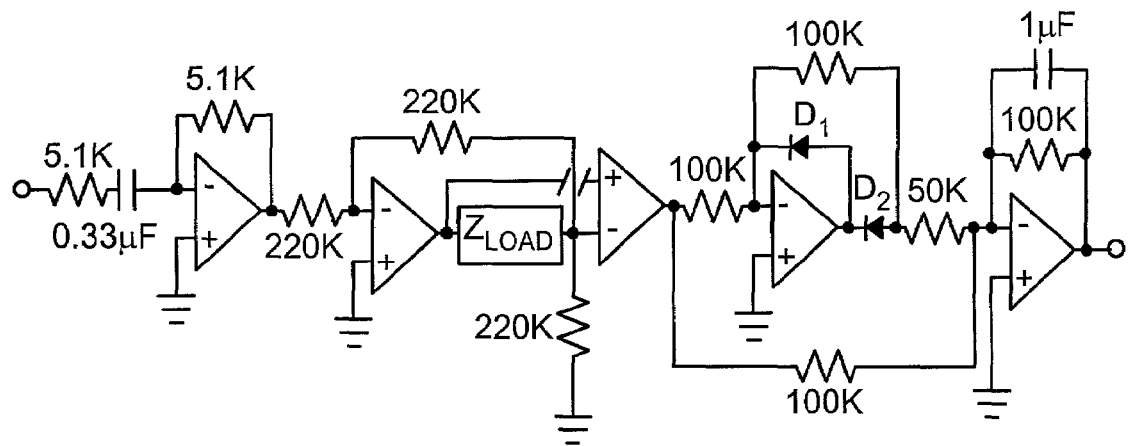
FIG. 8B is a schematic diagram of a circuit used for the impedance sensor in accordance with the invention.

In particular, as illustrated in FIG. 8A, a low voltage circuit is formed with two of the microneedles 14 acting as electrodes. Because the dry stratum corneum of the epidermis 90 acts as a capacitive barrier while the sub-epidermal layers 92 are well conducting, the impedance of the circuit drops as the microneedles pierce through the stratum corneum 90. The change in impedance is by one or more orders of magnitude and reliably indicates when the microneedles have pierced through the stratum corneum 90. Furthermore, at less than 1 Volt, the voltage stimulus is not felt by the subject. Note that the microneedles 14 are electrically isolated from the base. An illustrative embodiment of a circuit diagram of the circuit used here is shown in FIG. 8B, where the $Z_{load}$ represents the unknown impedance.

Figure 9A:
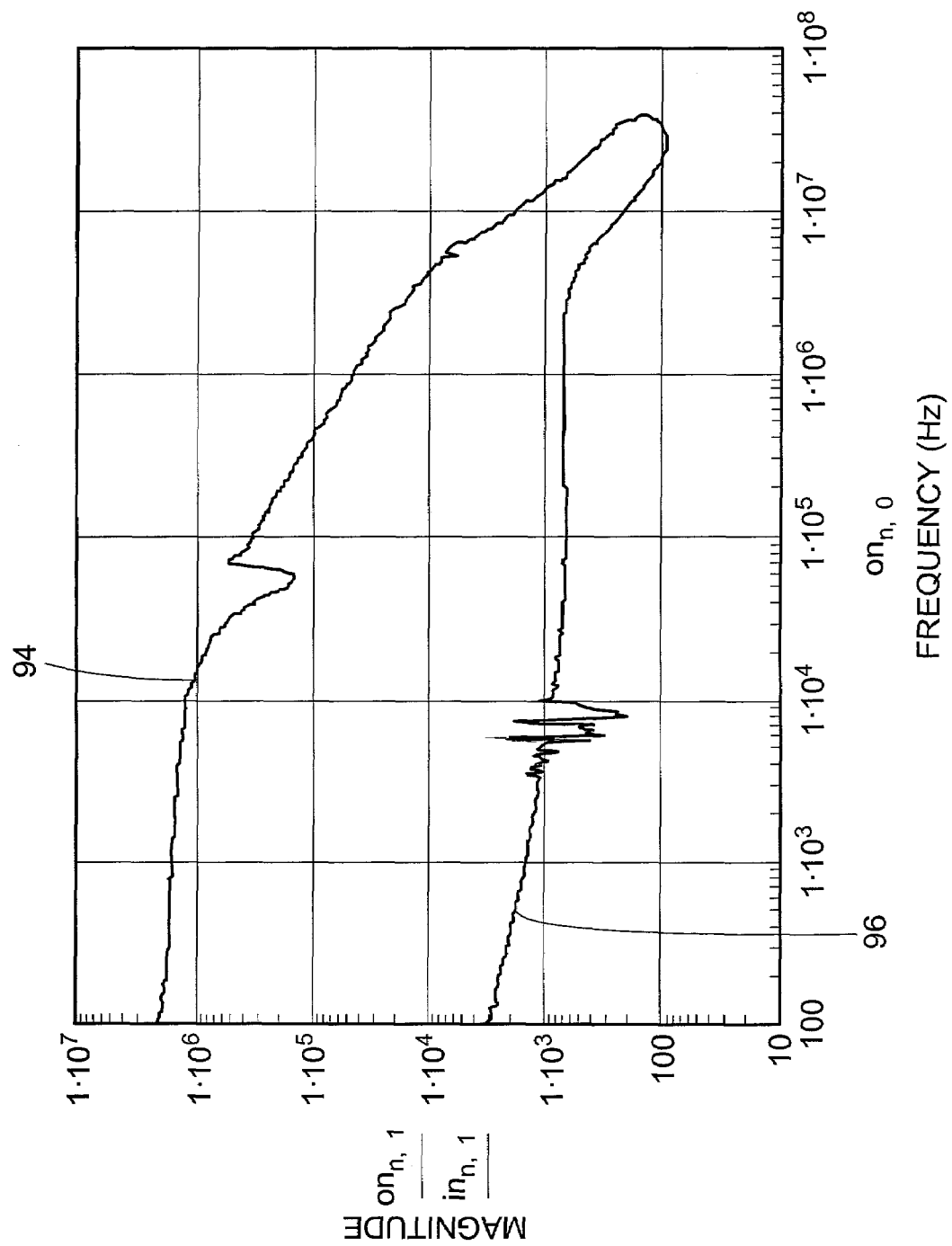
FIG. 9A is a graph of the magnitude of the impedance measured by the impedance sensor of FIG. 8A versus frequency.
Figure 9B:
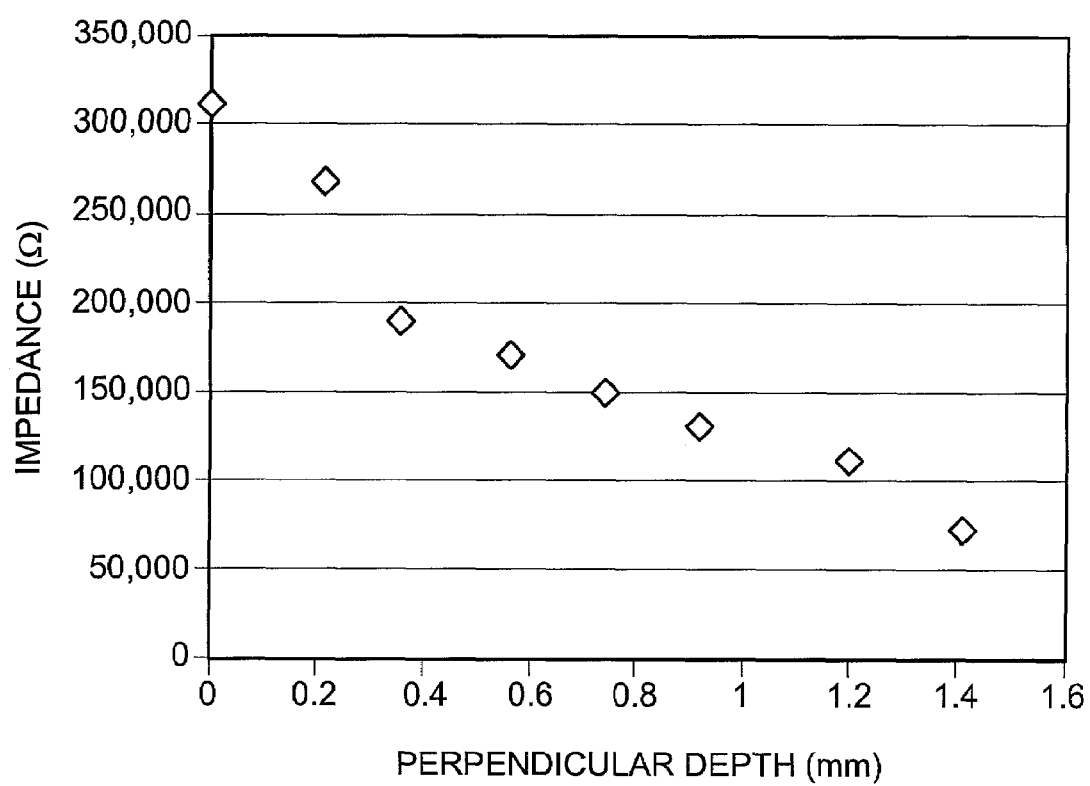
FIG. 9B is a graph of the impedance versus the penetration depth.

As an example, impedance measurements of pig skin is illustrated in FIG. 9A. The top portion 94 of the graph illustrates the measured impedance of pig skin over a frequency range before a microneedle penetrates the stratum corneum and the bottom portion 96 represents the measured impedance after the microneedle has penetrated the stratum corneum. As can be seen, the difference between the two portions 94 and 96 of the graph can be over three orders of magnitude. Turning also to FIG. 9B, there is shown a plot of impedance versus the perpendicular depth into the skin, which clearly illustrate that the penetration into the skin produces smaller impedances.

Rather than sweeping over a frequency range, the input signal of the impedance sensor 32 can be set at one frequency. The input signal can be a square wave generated by an embedded processor such as a TI-MSP430F149IPM, produced by Texas Instruments of Dallas, Tex. Certain characteristics of this chip are that it draws 35 μA when active, and less than 1 μA in low power mode, and has a 64 pin PQFP package, a 1.8 to 3.6 V power supply, 8 analog to digital converters, 60 kbytes of flash memory, 2 kbytes of RAM, 2 16-bit timers, and an on-chip comparator. Alternatively, a processor such as a TI-MSP430F110IPW can be used. This chip draws 35 μA when active, and less than 1 μA in low power mode, and includes a 20 pin TSSOP, 1.8 to 3.6 V power supply, 1 kbyte of flash memory, 128 bytes of RAM, and a 16-bit timer. Regardless which processor is used, the output signal can be pulse width modulated, and the impedance sensor 32 can be provided with a log transformer to compress the output signal to within the range of the analog to digital converter of the processor.

As mentioned earlier, in certain embodiments, a glucose sensor is associated with the transport device 10. In these embodiments, fluid is withdrawn from the patient through the microneedles 14 into one of a multiplicity of reservoir chambers. The glucose sensor is at least partially in one of the chambers, where it can detect the concentration of glucose in the fluid. Information from the glucose sensor is read and interpreted by the operator of the device 10, for example, with the use of the display 22 of the applicator 12, who can then activate another chamber of the reservoir to deliver the appropriate amount of insulin to bring the glucose concentration to an appropriate level. Alternatively, the procedure can be automated so that the glucose sensor reads the glucose concentration in the fluid, and, based on that concentration, sends a signal, such as an electronic signal, to the other chamber, "telling" that chamber whether or not to deliver insulin through a set of microneedles, and how much insulin to deliver.

In any of the above describe embodiments, one or more controllers such as a programmable microprocessor located in the transport device 10 and/or the applicator 12 can control and coordinate the actuators, pumps, sensors, and oscillators. For example, the controller can instruct the actuator 52 to pump a specified amount of drug into a patient at a specified time. The specified amount may be the full amount contained in the reservoir 46 or a partial amount. Thus, the device is able to inject a partial or full amount of drug incrementally over a desired time period. One controller may control the operation of the applicator 12, while another controller controls the operation of the device 10. Alternatively, a single controller may control the operations of the applicator 12 and the device 10. In any case, the applicator 12 and/or the device 10 can communicate with each other or with a central processor, for instance, using wireless communications capabilities provided with either or both the applicator 12 and the device 10.

The transdermal transport device 10 is not limited to the embodiments described above. For example, other embodiments of the transdermal transport device 10 are shown in FIGS. 10 and 11, where like reference numerals identify like features.

In the device 10 of FIG. 10, the microneedles 14 are again bent at about a 90° angle. They are oriented so that there is a section that is parallel to the surface of the skin S and a section that is perpendicular to the base 36 of the device 10. The microneedles 14 are soldered or attached in any suitable manner to a needle plate 100 that is able to turn, but not able to translate. In this embodiment, the microneedles 41 are not inserted into the drug vial 40 until just before delivery. The pump assembly or actuator 52 is pinned in place by three pins that slide in angled slots 101 as the inner portion of the device 10 is turned. For extra guidance and stability, the actuator 52 also rides on pins 102 in slots that are cut into the actuator 52.

The device 10 is first brought to the skin S by the applicator 12 (FIG. 1). The electromagnet 26 in the applicator 12 turns the inside portion of the device 10, which causes the actuator 52 to translate down onto the ends 64 of the microneedles 14 as the needles are turned into the skin S while suction is being applied through the ports 14 to draw the skin S into the suction ports 60. Thus, the back ends 64 of the microneedles penetrate the vial 40 as the front ends penetrate the skin. Alternatively, the back ends 64 of the microneedles can already be in the vial 40, while the front ends are provided with caps through which the needles penetrate, or are removed before inserting the needles into the skin. The drug in the reservoir 46 is then pumped through the microneedles 14 as the actuator 52 is activated.

The depth of insertion is controlled by hard stops 104 on the base plate 36. The skin S is sucked into the suction ports 60 by vacuum up to these hard stops 104. Since the microneedles 14 soldered into place at a specific depth, and the hard stops can be set to a desired distance from the plane of the needles, the depth of insertion can therefore be controlled.

The actuator 52 is mounted on top of the vial 40, with the flexible membrane 48 positioned between the two. The electrodes 72 are mounted inside the actuator 52, and the leads come out directly into a circuit board 106, which is mounted just above the top of the actuator 52. On the underside of the circuit board 106 are mounted the electronic components 43, and on the top side is mounted the battery or power source 45. The applicator 12 magnetically attaches to the battery 45 to hold and rotate the device 10, while electrical connection is made between the applicator 12 and the device 10 through the copper ring 42.

The device 10 of FIG. 10 has a height of about 15 mm, while the device 10 of FIG. 11 has a lower profile with a height of about 7 mm. In FIG. 11, the microneedles 14 are mounted such that they always remain in the same plane of rotation. This helps reduce the overall height of the device 10, since open space between the ends 64 of the microneedles 14 and the drug vial 40 is not necessary. The microneedles 14 can either be permanently affixed as part of the drug vial 40, or as a separate ring. If the microneedles 14 are mounted on a separate ring, the actuator 52 is rotated onto the back end 64 of the microneedles 14 before delivery. Then, the entire actuator/microneedle assembly is rotated into the skin S.

The depth of insertion is controlled by the space 200 between the base 36 and the component 202 that couples the microneedles 14 to the vial 40. This component 202 could either be some sort of fluidic circuit or simply a ring that holds the microneedles 14 in place for insertion into the vial 40, or the microneedles may be part of the vial 40. Vacuum suction would still be used to draw the skin into the ports 60 before insertion of the microneedles 14.

The actuator 52 is mounted as a ring around the vial 40. The top portion 204 of the actuator 52 is still above the vial 40, and the flexible membrane 48 is located between the top portion 204 and the vial 40. However, most of the actuator 52 is placed round the outside of the vial 40. This helps reduce the overall height of the device 10. The electrodes can be mounted as ring electrodes directly from the circuit board 106, which can also function as the top of the actuator 52. The battery 45 and the electronic components 43 are all mounted on the top of the circuit board 106.

While this invention has been particularly shown and described with references to preferred embodiments thereof, it will be understood by those skilled in the art that various changes in form and details may be made therein without departing from the scope of the invention encompassed by the appended claims. For example, the actuator or pump arrangements, such as the electrolytic actuator, can be used in other types of transdermal transport devices, as well, such as the devices described in the U.S. application Ser. No. 10/238,844, filed Sep. 9, 2002, by Angel and Hunter, the entire contents of which are incorporated herein by reference.

What is claimed is:

1. A transport device for transporting a substance through a surface of a body, comprising:
   a plurality of needles configured substantially parallel to the surface of the body to independently and removably secure the device to the surface of the body, each of the needles having a bore therethrough for transporting the substance to a target area of the body and at least two of the plurality of needles each piercing the body surface from a different respective direction; and
   an actuator which transports the substance through at least one of the plurality of needles and through the surface of the body.

2. The transport device of claim 1, further comprising means for moving a first and second respective portions of the body surface wherein a first needle of the plurality of needles substantially laterally pierces the first respective moved portion of the body surface, but not the second moved portion, and the second needle of the plurality of needles substantially laterally pierces the second moved portion of the body surface, but not the first moved portion.

3. The transport device of claim 2, wherein the moving means comprises a vacuum.

4. The transport device of claim 2, wherein each of the first and second needles substantially laterally pierces its respective moved portion from a different respective direction.

5. The transport device of claim 2, wherein the means for moving comprises a means for raising the first and second respective portions of the body surface.

6. The transport device of claim 2, wherein the different respective directions differ by a nonzero angle.

7. The transport device of claim 2 further comprising a controller which controls the device.

8. The transport device of claim 1 wherein the actuator transports the substance into the biological body.

9. The transport device of claim 1 wherein the actuator transports the substance from the body to a reservoir.

10. The transport device of claim 1 wherein the plurality of needles are positioned in a retracted state when the actuator is de-energized.

11. The transport device of claim 1 further comprising an oscillator which causes at least one of the plurality of needles to vibrate along its length to reduce the force required to drive the needle into the body.

12. The transport device of claim 1 further comprising a sensor to monitor the status of a patient.

13. The transport device of claim 12 wherein the status is a glucose concentration.

14. The transport device of claim 13 wherein the substance that the actuator translates through the surface is insulin and wherein an amount of insulin is based on the glucose concentration.

15. The transport device of claim 1 further comprising a base unit and a control unit separable from each other, the plurality of needles and actuator being located within the base unit, the first and second moved portions being at least partially moved within the base unit.

16. The transport device of claim 1 wherein at least one of the plurality of needles defines an opening through which the substance is transported, the opening being directed towards the body surface.

17. The transport device of claim 1 further comprising a controller which controls the device.

18. The transport device of claim 1 wherein each of the plurality of needles has a respective outer diameter of less than about 250 μm.

19. The transport device of claim 1 wherein each of the plurality of needles has a respective inner diameter of less than about 100 μm.

20. The transport device of claim 1 wherein each of the plurality of needles includes a bend.

21. The transport device of claim 1, wherein the actuator transports the substance through at least two needles.

22. The transport device of claim 1, further comprising a reservoir for holding the substance.

23. The transport device of claim 1 wherein at least two of the plurality of needles each pierce the body surface from a different respective direction.

24. The transport device of claim 1 wherein three or more of the plurality of needles each pierce a respective portion of the body surface from a different respective direction.

25. The transport device of claim 1, further comprising a plurality of guide sleeves, each of the plurality of needles guidable within a respective one of the guide sleeves through which the needle is guided into the skin.

26. The transport device of claim 1, further comprising an actuator to move the plurality of needles out of the body to disengage the delivery device from the body surface.

27. A transport device for transporting a substance through a surface of a body, comprising:
    a plurality of needles configured to attach the device to the surface of the body; and
    an actuator which transports the substance through at least one of the plurality of needles and through the surface of the body and moves at least one of the plurality of needles around an axis.

28. The transport device of claim 27, wherein the at least one needle is moved rotationally around an axis to substantially laterally pierce a respective portion of the surface.

29. The transport device of claim 27, wherein at least two of the plurality of needles are moved by a rotary actuator to substantially laterally pierce a respective first and second portions of the surface.

30. The transport device of claim 27 wherein the rotary actuator moves an end portion of at least one of the plurality of needles in a plane substantially parallel to the surface.

31. The transport device of claim 27 wherein the actuator rotates each of the plurality of needles about an axis.

32. A transport device for delivering a substance to a body having a surface, comprising:
    a reservoir for holding the substance;
    a needle configured to independently secure the device to the body, and through which the substance is transported between the reservoir and the body;
    an actuator which transports the substance between the reservoir and the body;
    a sensor that measures a status of the body; and
    a controller which directs the actuator to transport a desired amount of the substance, the desired amount being dependent on the measured status.

33. The transport device of claim 32 wherein the desired amount of the substance is delivered over a particular time period.

34. The transport device of claim 33, wherein the time period is more than one day.

35. The transport device of claim 33 wherein the time period is more than 1 sec.

36. The transport device of claim 32 wherein the desired amount of the substance is delivered incrementally over time.

37. The transport device of claim 32 wherein the body is a human patient.

38. The transport device of claim 32 wherein one or more of the plurality of needles collects a sample from the body, the sensor measuring the collected sample.

39. The transport device of claim 32, wherein the surface is skin.

40. A method of transporting a substance, comprising:
    placing a delivery device with a reservoir for holding the substance on a body surface of a biological body;
    inserting a plurality of needles into the body, the plurality of needles configured substantially parallel to the surface of the body to independently secure the device to the body surface and at least two of the plurality of needles each piercing the body surface from a different respective direction;

transporting the substance through a bore of at least one of the plurality of needles between a target area of the body and the reservoir; and controlling the transporting of the substance being dependent on a status of the body.

41. A substance transport device, comprising:

means for holding a substance;

needle means for independently securing the device to a surface of a body;

means for transporting the substance between the means for holding and a target area of the body; and means for transporting the substance between the target area of the body and the first end of the means for holding.

42. A transport device for transporting a substance through a surface of a body, comprising:

a plurality of needles configured to attach the device to the surface of the body and rotatable about an axis for attaching the device to the surface of the body; and an actuator which transports the substance through at least one of the plurality of needles and through the surface of the body.

43. A transport device for transporting a substance through a surface of a body, comprising:

a plurality of needles configured to attach the device to the surface of the body;

an actuator which transports the substance through at least one of the plurality of needles and through the surface of the body;

means for moving a first and second respective portions of the body surface wherein a first needle of the plurality of needles substantially laterally pierces the first respective moved portion of the body surface, but not the second moved portion, and the second needle of the plurality of needles substantially laterally pierces the second moved portion of the body surface, but not the first moved portion; and first and second ports into which first and second respective portions of the body surface are moved.

44. The transport device of claim 43, wherein the directions differ by a nonzero angle.

45. The transport device of claim 43, wherein the directions differ with respect to each other by an angle less than 180 degrees.

46. The transport device of claim 43, wherein each of the at least two needles pierces a different respective portion of the surface.

47. The transport device of claim 43, wherein each of the three or more needles pierces a different respective portion of the surface.

48. A transport device for delivering a substance to a body having a surface, comprising:

a reservoir for holding the substance;

a needle configured to attach the device to the body, and through which the substance is transported between the reservoir and the body;

an actuator which transports the substance between the reservoir and the body;

a sensor that measures a status of the body;

a controller which directs the actuator to transport a desired amount of the substance, the desired amount being dependent on the measured status; and a second needle which pierces the surface of the body at a different respective angle from the first needle.

49. A method of transporting a substance, comprising:

placing a delivery device with a reservoir for holding the substance on a body surface of a biological body;

inserting a plurality of needles into the body, the plurality of needles configured substantially parallel to the surface of the body to removably attach the device to the body surface, at least two of the plurality of needles each piercing the body surface from a different respective direction;

transporting the substance through a bore of at least one of the plurality of needles between a target area of the body and the reservoir; and controlling the transporting of the substance being dependent on a status of the body.

50. A substance transport device, comprising:

means for holding a substance;

needle means for attaching the device to a surface of a body;

means for transporting the substance between the means for holding and a target area of the body; and means for transporting the substance between the target area of the body and the first end of the means for holding;

a second needle means which pierces the surface of the body at a different respective angle from the first needle means.

* * * * *